US008987556B2

(12) United States Patent
Datta et al.

(10) Patent No.: US 8,987,556 B2
(45) Date of Patent: Mar. 24, 2015

(54) POLYNUCLEOTIDE SEQUENCE OF FRUIT SOFTENING ASSOCIATED β-D-N-ACETYLHEXOSAMINIDASE AND ITS USES FOR ENHANCING FRUIT SHELF LIFE

(75) Inventors: Asis Datta, New Delhi (IN); Subhra Chakraborty, New Delhi (IN); Niranjan Chakraborty, New Delhi (IN); Vijaykumar Meli Siddesh, New Delhi (IN); Sumit Ghosh, New Delhi (IN)

(73) Assignee: National Institute of Plant Genome Research, New Delhi (IN)

( * ) Notice: Subject to any disclaimer, the term of this patent is extended or adjusted under 35 U.S.C. 154(b) by 384 days.

(21) Appl. No.: 13/003,051

(22) PCT Filed: Jul. 9, 2009

(86) PCT No.: PCT/IN2009/000388
§ 371 (c)(1),
(2), (4) Date: Jun. 30, 2011

(87) PCT Pub. No.: WO2010/004583
PCT Pub. Date: Jan. 14, 2010

(65) Prior Publication Data
US 2011/0258739 A1    Oct. 20, 2011

(30) Foreign Application Priority Data
Jul. 9, 2008   (IN) .......................... 1648/DEL/2008

(51) Int. Cl.
*C07H 21/04* (2006.01)
*C12N 15/82* (2006.01)
*C12N 1/21* (2006.01)
*C12N 15/113* (2010.01)
*A01H 5/00* (2006.01)
*C12N 9/24* (2006.01)

(52) U.S. Cl.
CPC ..... *C12N 15/8249* (2013.01); *C12Y 302/01052* (2013.01); *C12N 9/2402* (2013.01)
USPC ...... 800/286; 536/23.2; 536/24.5; 435/320.1; 435/252.3; 800/285; 800/298; 800/317.4

(58) Field of Classification Search
None
See application file for complete search history.

(56) References Cited

PUBLICATIONS

Jagadeesh et al, 2004, Plant science, 166:1451-1459.*
Strasser et al, 2007, Plant Physiol., 145:5-16.*
Xiong et al, 2005, Plant Cell Rep., 23:639-646.*
Jagadeesh, B. et al. "Multiple Forms of β-Hexosaminidase in Ripening Tomato (*Lycopersicum Esculantum* L.)", Indian J. Plant Physiol., vol. 11, No. Jan.-Mar. 2006, pp. 13-19.
Jagadeesh, B. et al. "Activities of glycosidases during fruit development and ripening of tomato (*Lycopersicum Esculantum* L.): implication in fruit ripening", Plant Science, vol. 166, 2004, pp. 1451-1459.
Jagadeesh, B. et al. "β-Hexosaminidase, an enzyme from ripening bell capsicum (*Capsicum annuum* var. *variata*)", Phytochemistry, vol. 61, 2002, pp. 295-300.
Jin, Y. et al. "Purification and Characterization of β-N-Acetylhexosaminidase from Rice Seeds", Journal of Biochemistry and Molecular Biology, vol. 35, No. 3, May 2002, pp. 313-319.
Database UniProt 2000, Theologis, A. et al. "Sequence and analysis of chromosome 1 of the planet Arabidopsis thaliana" XP002558282, retrieved from EBI Database accession No. Q9SYKO.
Orzaez, D. et al. "Agroinjection of Tomato Fruits. A Tool for Rapid Functional Analysis of Transgenes Directly in Fruit", Plant Physiology, vol. 140, Jan. 2006, pp. 3-11.
Brummell, D. et al. "Cell wall metabolism in fruit softening and quality and it manipulation in transgenic plants", Plant Molecular Biology, vol. 47, 2001, pp. 311-340.
Wesley, S. "Construct design for efficient, effective and high throughput gene silencing in plants", The Plant Journal, vol. 27, No. 6, 2001, pp. 581-590.
Strasser, R. et al. "Enzymatic Properties and Subcellular Localization of Arabidopsis β-N-Acetylhexosaminidases", Plant Physiology, vol. 145, Sep. 2007, pp. 5-16.
Giovannoni, J. "Molecular Biology of Fruit Maturation and Ripening", Annu. Rev. Plant Physiol. Mol. Biol., vol. 52, 2001, pp. 725-749.
Priem, B. et al. "Structure of Ten Free *N*-Glycans in Ripening Tomato Fruit", Plant Physiology, vol. 102, 1993, pp. 445-458.

* cited by examiner

*Primary Examiner* — Ashwin Mehta
*Assistant Examiner* — Jason Deveau Rosen
(74) *Attorney, Agent, or Firm* — Merchant & Gould P.C.

(57) ABSTRACT

The present invention provides isolated polynucleotide sequences encoding β-D-N-acetylhexosaminidase. The present invention further provides DNA construct comprising the polynucleotide sequence coding for β-D-N-acetylhexosaminidase in sense or antisense orientation, RNAi construct, recombinant vector comprising the construct and host cells comprising the recombinant vector disclosed in the present invention. The present invention further provides transgenic plant, plant cell, transgenic progeny and seeds expressing the polynucleotide with reduced β-D-N-acetylhexosaminidase protein accumulation, having enhanced fruit shelf life.

18 Claims, 5 Drawing Sheets

POLYNUCLEOTIDE SEQUENCE OF FRUIT SOFTENING ASSOCIATED B-D- N -ACETYLHEXOSAMINIDASE AND ITS USES FOR ENHANCING FRUIT SHELF LIFE

This application is a National Stage Application of PCT/IN2009/000388, filed 9 Jul. 2009, which claims benefit of Serial No. 1648//DEL/2008, filed 9 Jul. 2008 in India and which applications are incorporated herein by reference. To the extent appropriate, a claim of priority is made to each of the above disclosed applications.

FIELD OF INVENTION

The present invention relates to isolated polynucleotides coding for fruit softening associated enzyme, β-D-N-acetylhexosaminidase from plants.

BACKGROUND OF THE INVENTION

The post-harvest losses of fruits and vegetables, which are quickly perishable, are a major cause for concern in developing countries because of the fact that a large amount of what is produced never reaches to the consumer. This loss in India, the second largest producer of fruits and vegetables, account for 35-40% of total produce; a loss estimated at 40,000 crores per year, directly affecting economy. The main factor in determining the post-harvest deterioration of fruit and vegetable crops is the rate of softening, which influences shelf life, wastage, infection by post-harvest pathogens, frequency of harvest, and limits transportation and storage, all of which directly affect costs. Attempts to understand molecular basis softening is focused on cell wall metabolism and tomato has provided the principal model system for these studies. However, decreased expression of several proteins acting on cellulose, hemicelluloses and pectin polysaccharides in transgenic tomato fruit has proven to be insufficient to prevent fruit softening [Brummell D A, Harpster M H (2001) Plant Mol Biol. 47:311-340 and Giovannoni J (2001) Annual Review of Plant Physiology and Plant Molecular Biology 52: 725-749], suggesting that modifications of these cell wall components are not the sole factors to determine fruit firmness.

N-Glycoproteins are one of the constituents of plant cell wall and free N-glycans are also reported to occur in tomato fruit. Moreover free N-glycans are known to induce tomato fruit ripening and blocking of N-glycosylation with tunicamycin delayed fruit ripening, which suggests that N-glycoprotein processing is important in ripening process [Priem B, Gitti R, Bush C A, and Gross K C (1993) Plant Physiol. 102: 445-458]. Most glycoprotein of plant source contain substantial amount of paucimannosidic N-glycans, which is produced by the removal of terminal GlcNAc residues in the secretory pathway as a consequence of β-D-N-acetylhexosaminidase activity (Strasser R, Bondili J S, Schoberer J, Svoboda B, Liebminger E, Glossl J, Altmann F, Steinkellner H and Lukas Mach (2007) Plant Physiology 145: 5-16.). Moreover, β-D-N-acetylhexosaminidase shows consistent increase in activity during ripening of tomato and capsicum and is present in banana, mango, papaya, etc. (Jagadeesh B H and Prabha T N (2002) Phytochemistry, 61(3): 295-300; and Jagadeesh B H, Prabha T N and Srinivasan K (2004) Plant Science 166(6): 1451-1459).

SUMMARY OF THE INVENTION

The present invention relates to purification and characterization of fruit softening associated enzyme, β-D-N-acetyl- hexosaminidase of tomato (*Solanum lycopersicum*) and capsicum (*Capsicum annuum*). The present invention also relates to identification, isolation and cloning of tomato and capsicum β-D-N-acetylhexosaminidase genes. The present invention further relates to transgenic plants, with reduced β-D-N-acetylhexosaminidase protein accumulation, having enhanced fruit shelf life.

One aspect of the present invention provides an isolated polynucleotide encoding a polypeptide having hexosaminidase activity, wherein the nucleotide sequence of said polynucleotide encodes a polypeptide having at least about 85% identity with an amino acid sequence as set forth in SEQ ID NO: 3 or SEQ ID NO: 5.

Another aspect of the present invention provides a polypeptide having amino acid sequence as set forth in SEQ ID NO: 3 or SEQ ID NO: 5.

Yet another aspect of the present invention provides an RNAi construct for suppressing expression of hexosaminidase in a transgenic plant, the construct comprising a sense polynucleotide strand comprising at least 20 contiguous nucleotides from the sequence as set forth in SEQ ID NO: 2 or SEQ ID NO: 4, and an antisense polynucleotide strand that hybridizes to said sense polynucleotide strand, wherein the antisense polynucleotide strand and the sense polynucleotide strand form a duplex.

Yet another aspect of the present invention provides a process for delaying fruit softening in plant, the process comprising transforming a plant cell, tissue or any part thereof with the recombinant vector comprising the polynucleotide encoding a polypeptide having hexosaminidase activity, wherein the nucleotide sequence of the polynucleotide encodes a polypeptide having at least about 85% identity with an amino acid sequence as set forth in SEQ ID NO: 3 or SEQ ID NO: 5, wherein the polynucleotide is in anti-sense orientation.

Yet another aspect of the present invention provides a process for delaying fruit softening in plant, the process comprising decreasing the level of hexosaminidase in transgenic plant compared to its level in non-transgenic plant by expression of an RNA interference (RNAi) construct comprising at least a fragment of at least 20 contiguous nucleotides of the polynucleotide encoding a polypeptide having hexosaminidase activity, wherein the nucleotide sequence of the polynucleotide encodes a polypeptide having at least about 85% identity with an amino acid sequence as set forth in SEQ ID NO: 3 or SEQ ID NO: 5; and screening the resulting plants for reduced level of hexosaminidase relative to the non-transgenic plant.

Yet another aspect of the present invention provides a process for delaying fruit softening in plant, the process comprising decreasing the level of hexosaminidase in transgenic plant compared to its level in non-transgenic plant by expression of an RNA interference (RNAi) construct comprising a sense polynucleotide strand comprising at least 20 contiguous nucleotides from the sequence as set forth in SEQ ID NO: 2 or SEQ ID NO: 4, and an antisense polynucleotide strand that hybridizes to the sense polynucleotide strand, wherein the antisense polynucleotide strand and the sense polynucleotide strand form a duplex; and screening the resulting plants for reduced level of hexosaminidase relative to the non-transgenic plant.

Still yet another aspect of the present invention there is provided a transgenic plant, seed or progeny thereof, wherein expression of the hexosaminidase in the plant is controlled to delay fruit softening.

BRIEF DESCRIPTION OF ACCOMPANYING DRAWINGS

The above and other features, aspects, and advantages of the subject matter will become better understood with regard to the following description, appended claims, and accompanying drawings.

FIG. 1 shows

A) β-D-N-acetylhexosaminidase activity during tomato fruit ripening. Data are mean±s.e.m., n=4. MG—matured green, B—breaker, P—pink, RR—red ripe.

B) 6% non-denaturing PAGE analysis of purified β-D-N-acetylhexosaminidase protein from tomato.

C) 6% non-denaturing PAGE analysis of purified β-D-N-acetylhexosaminidase protein from capsicum.

D) tomato β-D-N-acetylhexosaminidase activity on N-glycan substrates. N-glycan1 and N-glycan2 are biantennary N-linked core pentasaccharide and asialo, agalacto, biantennary, respectively.

E) β-D-N-acetylhexosaminidase activity during capsicum fruit development and ripening stages. Activity checked in eight stages (S1-S8).

F) 2DE analysis of tomato purified protein. Spots 1, 2 and 3 were identified as SlHEX1.

G) 2DE analysis of capsicum purified protein. Spots 1, 2 and 3 were identified as CaHEXO1.

FIG. 2 shows

A) SlHEX1 gene expression during tomato fruit ripening as determined by quantitative Real Time reverse transcriptase PCR (qRT PCR) analysis. Data are mean±s.e.m., n=3

B) the protein level expression of SlHEX1, as determined by western blotting using peptide based antibody.

FIG. 3 shows

A) effect of transient silencing and over-expression of SlHEX1 in tomato fruit, by agroinjection, on β-D-N-acetylhexosaminidase activity. 5RH1 and 3RH1 are RNAi construct designed from 5' and 3' sequence of SlHEX1, respectively. 7FH1 represent overexpression of SlHEX1.

B) confirmation of gene silencing by northern blotting. C is control. (Empty vector injected)

C) confirmation of gene silencing by western blotting. '+Ve' denotes purified protein.

D) quantitative measurement of firmness of RNAi agro injected fruits 15 days after agroinjection. Data are mean±s.e.m., n=30, P<0.0001.

FIG. 4 shows

A) subcellular localization of SlHEX1. C-terminal GFP fusion protein was transiently expressed in tomato fruit by agroinjection. GFP signal was observed in the cell wall.

B) relative expression of SlHEX1 in ripening impaired mutants rin, nor and Nr compared to wild type (Ailsa craig) as determined by qRT PCR analysis. Data are mean±s.e.m., n=3.

C) ACC inducibility of the gene as determined by qRT PCR. Data are mean+s.e.m., n=3.

FIG. 5 shows

A) SlHEX1 transcript level and β-D-N-acetylhexosaminidase activity in $T_o$ fruits of SlHEX1 overexpression lines as determined by qRT PCR analysis and enzyme assay, respectively. C is control (wild type). Data are mean±s.e.m., n=3

B) SlHEX1 transcript level and enzyme activity in SlHEX1 RNAi/Antisense lines as determined by qRT PCR analysis and enzyme assay, respectively. Data are mean±s.e.m., n=3.

C) 5 mm compression analysis of fruits from SlHEX1 suppressed and overexpressed $T_o$ lines at different stages of ripening. Data are mean+s.e.m., n=15. OR—over ripe (Pink+ 10 days).

D) progression of post harvest fruit deterioration recorded by time lapse photography. Fruits from transgenic ($T_o$) and wild type plants were harvested at pink stage and stored at room temperature (22-24° C. in 55-60% relative humidity). Time after harvest is specified by days.

E) the section of pink and red ripe stage fruits stained with toluidine blue dye.

DETAILED DESCRIPTION OF THE INVENTION

The present invention relates to tomato and capsicum fruit softening associated β-D-N-acetylhexosaminidases. The instant invention particularly relates to polynucleotide sequence coding for β-D-N-acetylhexosaminidase, wherein RNAi and antisense mediated suppression of β-D-N-acetylhexosaminidase expression in plants delays fruit softening and overexpression enhances fruit softening.

The inventors of the present invention focused on the beneficial physiological functions of β-D-N-acetylhexosaminidases such as regulatory role in fruit softening. The present invention was conducted by taking such requirement into account, and its objective is to provide a method for delaying the fruit softening for enhancing the shelf life of fruit by reducing the levels of hexosaminidase in transgenic plant.

The instant invention provides the DNA constructs, recombinant vectors and recombinant host cells comprising the polynucleotide coding for the polypeptide having the β-D-N-acetylhexosaminidase activity. The instant invention further provide a method for delaying fruit softening in plants using the polynucleotide sequence of β-D-N-acetylhexosaminidase disclosed in the present invention. In addition the instant invention provides the transgenic plants, progeny and seed thereof, wherein suppression of β-D-N-acetylhexosaminidase in the plant is resulted in enhanced fruit shelf life.

The resultant transgenic plant obtained by the suppressing the expression β-D-N-acetylhexosaminidase gene using the antisense and RNAi technology produced fruits which were about 1.5 to 2 times firmer than the non transgenic fruits. Moreover the transgenic fruits produced by RNAi technology showed no signs of softening up to 45 days of harvest which is almost 30 days more than the non-transgenic fruits. The transgenic fruits produced by the antisense technology showed no signs of softening up to 35 days of harvest which is almost 20 days more than the non-transgenic fruits. These results are surprising and unexpected. In addition, suppression of the gene in transgenic plants had no negative effect on vegetative growth, flowering and fruit development, days to maturity and yield.

In one embodiment, the instant invention provides purification and biochemical characterization of β-D-N-acetylhexosaminidase enzyme from tomato and capsicum fruit pericarp and cloning of cDNA and genomic DNA of the corresponding genes from tomato and capsicum.

In another embodiment, the instant invention relates to studying the expression of the gene coding for the polypeptide having the β-D-N-acetylhexosaminidase activity in wild type and different tomato ripening impaired mutants. Furthermore, ethylene inducibility and cell wall localization of β-D-

N-acetylhexosaminidase protein was determined. In addition, the functional characterization of the gene was carried out by *Agrobacterium* mediated transient and stable transformation experiments.

Figure 1:
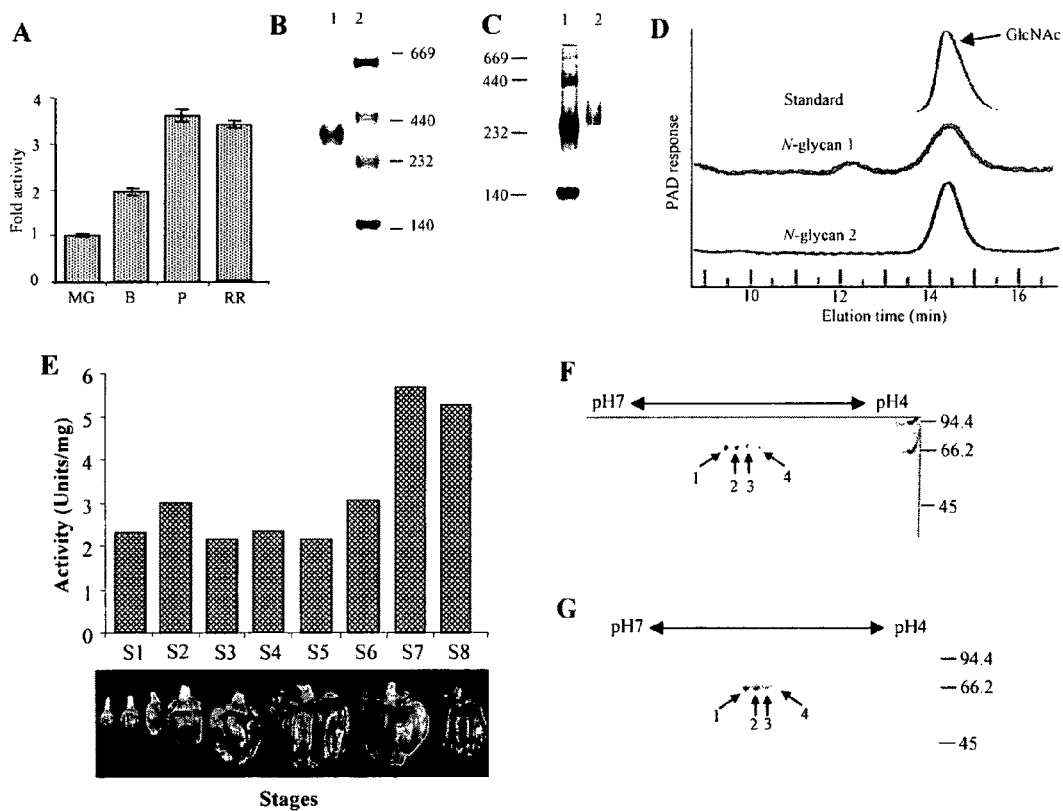

The enzyme exhibited ~3.5 fold enhancement of its specific activity during ripening of tomato fruit (FIG. 1A). Similarly, in capsicum the enzyme showed highest activity during fruit ripening (FIG. 1E). β-D-N-acetylhexosaminidase was purified from capsicum and tomato fruits to electrophoretic homogeneity from total protein extracted from fruit pericarp by subjecting ammonium sulphate precipitation, followed by ion exchange chromatography on DEAE Sepharose, affinity chromatography on ConA Sepharose and gel filtration chromatography on Sephadex G-100 column. The purified enzyme was a single polypeptide of 80 kDa on SDS-PAGE. However, the native size of the protein was 300 kDa on non-denaturing PAGE (FIG. 1B, C). β-D-N-acetylhexosaminidase is a glycoprotein as it was able to bind ConA Sepharose column and was positive with PAS staining. Biochemical characterization of tomato and capsicum hexosaminidase was carried out using pNP-N-acetyl-β-D glucosaminide (pNP-GlcNAc) substrate. The optimum pH and temperature for pNP-GlcNAc hydrolysis were pH6.0 and 45° C., respectively for both tomato and capsicum hexosaminidase and this enzyme was stable between wide ranges of pH (pH4.0-pH8.0 for tomato and pH3.0-pH9.0 for capsicum) without significant loss of activity. The tomato hexosaminidase could retain 90% of its activity at 37° C. for 60 min but was 50% inactive at 42° C. after incubation for 60 min. Capsicum hexosaminidase is stable at 42° C. for 60 min. Km was 0.225 mM for tomato hexosaminidase and 0.141 mM for capsicum hexosaminidase. N-glycans processing function of β-D-N-acetylhexosaminidase was determined by incubating 10 μg of N-glycan substrates at 37° C. for 12 hr with 0.5 μg of purified protein in a 100 μl reaction mixture. Then the sample was filtered through PVDF membrane to remove the protein and 10 μl of the filtered sample was loaded on to Carbopac PA-1 (4×250 mm) column and the release of GlcNAc was determined through high performance anion exchange chromatography (FIG. 1D). Two dimensional gel electrophoresis (2DE) of purified tomato protein revealed the presence of four polypeptides with different isoelectric points. Mass spectrometry (LC-MS/MS) analysis reveled that spot numbers 1, 2 and 3 are identical and it is named as *Solanum lycopersicum* β-D-N-acetylhexosaminidase1 (SlHEX1) (FIG. 1F). Further, 2DE of purified capsicum protein revealed similar pattern of polypeptide separation (FIG. 1G). Spots 1, 2 and 3 are depicted similar polypeptide and named as *Capsicum annum* β-D-N-acetylhexosaminidase1 (CaHEXO1).

On the basis of peptide sequence obtained from mass spectrometry analysis and conserved motifs identified from multiple sequence alignment of *Arabidopsis* and rice β-D-N-acetylhexosaminidases, we designed degenerate gene specific oligonucleotides that were used to clone SlHEX1 from tomato and CaHEXO1 from *capsicum* through rapid amplification of cDNA ends. Total RNA was isolated from fruit pericarp of tomato and reverse transcribed to generate cDNA using polyA tail specific oligonucleotide (RACE adapter primer-5' GGCCACGCGTCGACTAG-TACTTTTTTTTTTTTTTTT 3'-SEQ ID NO: 6). A gene specific degenerate primer corresponding to the peptide KLNVLHWH (5' AARYTIAATGTTYTICAYTGGCA 3'-SEQ ID NO: 7) and a nested primer derived from RACE adapter primer (5' GGCCACGCGTCGACTAGTAC 3'-SEQ ID NO: 8) were able to amplify DNA fragments which were cloned into pGEM-T Easy vector and sequenced. Analysis of the derived sequences by BlastX identified as partial sequences of SlHEX1. The gene belongs to glycosyl hydrolase family 20 (CaZy family). Further, RACE PCR (Invitrogen) was performed to determine the 5' end sequence of the gene. Using similar approach CaHEXO1 gene of *capsicum* was cloned.

Figure 2:
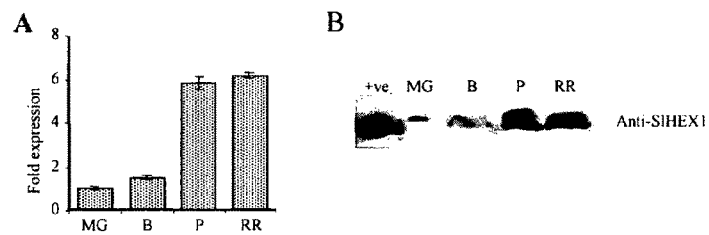

Quantitative Real Time PCR (qRT PCR) analysis revealed the appearance of ~6 fold more transcripts for tomato SlHEX1 in pink and red ripe fruits compared to mature green fruits (FIG. 2A). Protein accumulation pattern as determined by western blotting analysis using peptide-based antibody raised against SlHEX1 protein was similar to mRNA expression (FIG. 2B). The nature SlHEX1 gene expression pattern, during fruit ripening, correlates with β-D-N-acetylhexosaminidase activity.

Figure 3:
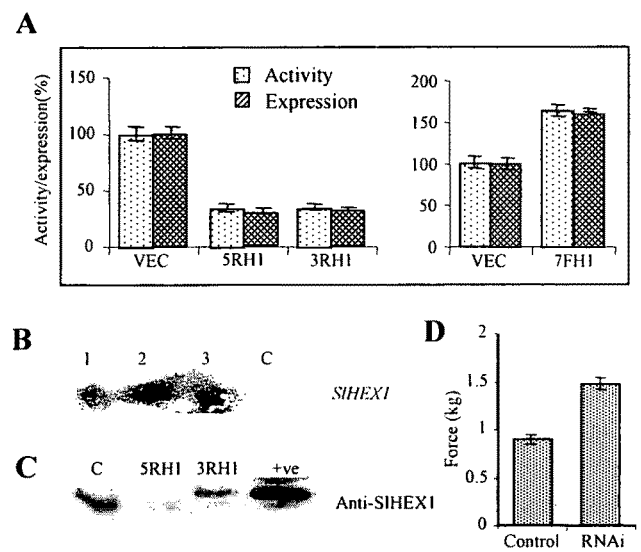
Figure 4:
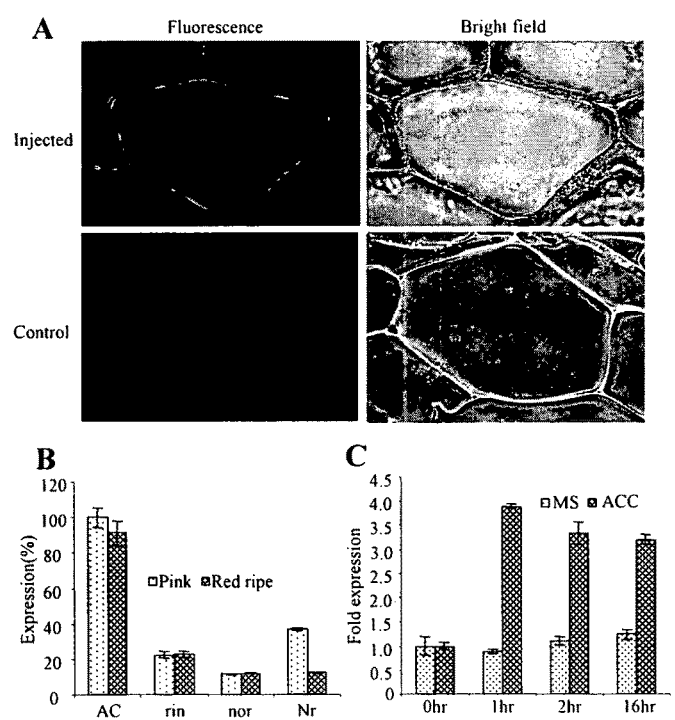
Figure 6:
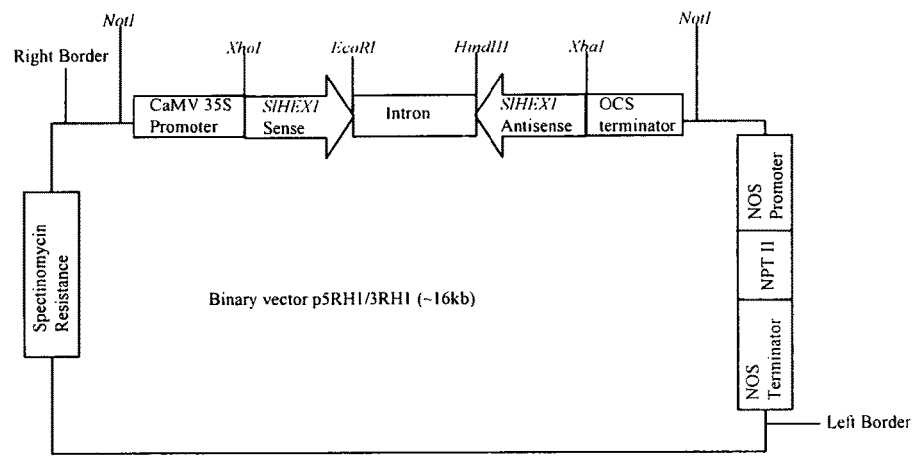
FIG. 6 shows diagram of recombinant vectors (p5RH1 and p3RH1) used to generate RNAi lines.
Figure 7:
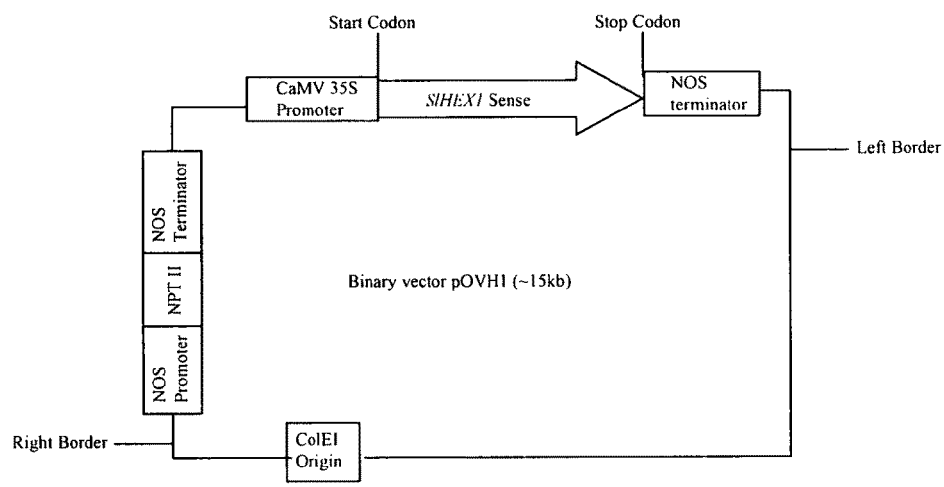
FIG. 7 shows diagram of recombinant vector (pOVH1) used to generate overexpression lines.
Figure 9:
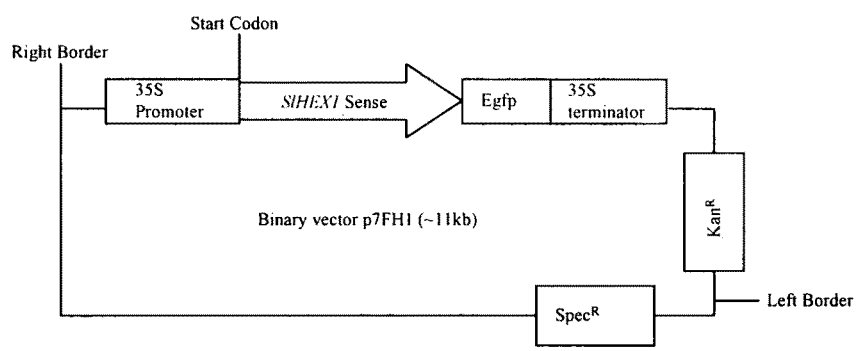
FIG. 9 shows diagram of recombinant vector (p7FH1) used for transient overexpression and subcellular localization experiments.

To develop RNAi constructs for SlHEX1, 600 bp 5' or 3' coding region of the gene including the respective UTRs was cloned into pHANNIBAL (Wesley S V, Helliwell C A, Smith N A, Wang M B, Rouse D T, Liu Q, Gooding P S, Singh S P, Abbott D, Stoutjesdijk P A, Robinson S P, Gleave A P, Green A G and Waterhouse P M (2001) Plant J 27: 581-590) in sense and antisense orientation separated by an intron. Finally, the NotI fragment of the construct was cloned into a binary vector, pART27 and named as p5RH1 (vector designed from 5' end sequence of SlHEX1) and p3RH1 (vector designed from 3' end sequence of SlHEX1) (FIG. 6). Over-expression constructs were developed either in gateway vector PK7FWG2, 0 or pBI121 vector (named as p7FH1 and pOVH1, FIGS. 7 and 9). Further, these binary vectors were mobilized to *Agrobacterium tumefaciens* strain EHA 105 by electroporation and grown up to mid log phase. Other *Agrobacterium* strains which can be used are LBA 4404, GV3101 etc. The grown *Agrobacterium* cells were collected and resuspended in infiltration media and agroinjected into the pericarp of the matured green tomato fruits. Injected fruits were harvested 3-5 days after injection at pink stage and analyzed for the reduction in transcript and protein level in RNAi injected fruits compared to empty vector injected fruits. Real Time PCR and western blot analysis showed reduction in mRNA and protein level, which was resulted in the loss of β-D-N-acetylhexosaminidase activity in the suppressed fruits (FIG. 3A, C). To determine whether this reduction of enzyme activity in RNAi injected fruits was due to the silencing of SlHEX1 gene expression, we checked the generation of gene specific small interfering (siRNA) in silenced fruits by northern hybridization. We could able to detect 21nt small RNAs specific to SlHEX1 in RNAi injected fruits (FIG. 3B). These observations again confirmed the correlation between SlHEX1 gene expression and enzyme activity. This gene was also transiently overexpressed in tomato fruit. For overexpression fruits were agroinjected at matured green stage and harvested at pink stage, where overexpression of SlHEX1 gene resulted in enhanced β-D-N-acetylhexosaminidase activity (FIG. 3A). To obtain a better understanding of SlHEX1 in fruit ripening its transcript accumulation was determined in tomato ripening impaired mutants rin, nor and Nr fruits. Since, mutant fruits do not undergo normal ripening process; comparison to wild type was made at the same chronological age rather than similar stages of ripening. qRT PCR analysis revealed reduction in SlHEX1 transcript level up to 78% in rin and 89% in nor at both pink and red ripe stages. However in case of Nr fruits transcript level was reduced up to 63% in pink stage and 88% in red ripe stage (FIG. 4B). All these mutations affect either ripening associated ethylene biosynthesis or ethylene perception and ultimately had reduced fruit softening. The lack of expression of SlHEX1 in these mutants strongly suggests its role in ripening related softening and its regulation by ethylene. The expression of SlHEX1 gene was ~4 fold upregulated in 0.1 mM ACC treated tomato seedlings which confirmed its ethylene regulation (FIG. 4C). Furthermore, the contribution of β-D-N-acetylhexosaminidase activity towards the ripening related loss of fruit firmness was determined by analyzing the rate of softening of SlHEX1 RNAi fruits by quantitative measurement of fruit firmness using Texture Analyzer (TA-XT plus, Stable Microsystem, UK). Agroinjected fruits were harvested at pink stage and stored at room temperature (22-24° C.) in 60-65% relative humidity. 5 mm compression analysis of intact RNAi and empty vector injected fruits was done 10 days after harvested which showed statistically significant difference in fruit firmness. RNAi injected fruits were ~1.6 times firmer than control fruits (FIG. 3D). To gain a detailed knowledge about its function and the site of action the subcellular location of SlHEX1 protein was determined. For this, GFP was fused to the C-terminal end of the protein using gateway vector pK7FWG2,0 and the fusion protein was transiently expressed in tomato fruit by agroinjection. Injection was done at mature green stage and harvested at pink stage. Injected fruits pericarp was sectioned in a cryostat and viewed under a fluorescence microscope with appropriate filter. GFP signal was detected in the cell wall region of the cell, confirming its localization in cell wall where it can act to cell wall glycoproteins (FIG. 4A).

Figure 8:
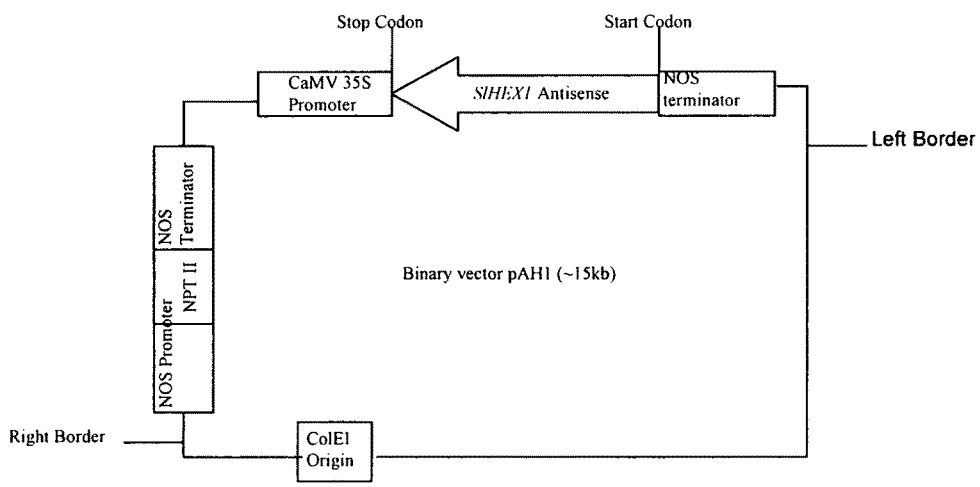
FIG. 8 shows diagram of recombinant vector (pAH1) used to generate antisense lines.

We used SlHEX1 gene to develop stably transformed suppression and overexpression lines in tomato. Two RNAi constructs, p5RH1 and p3RH1 were developed in pHANNIBAL using 600 bp 5' and 3' region of the gene, respectively (FIG. 6). Antisense and over-expression construct was generated in pBI121 after removing GUS coding sequence (named as pAH1 and pOVH1, FIGS. 7 and 8).

Figure 5:
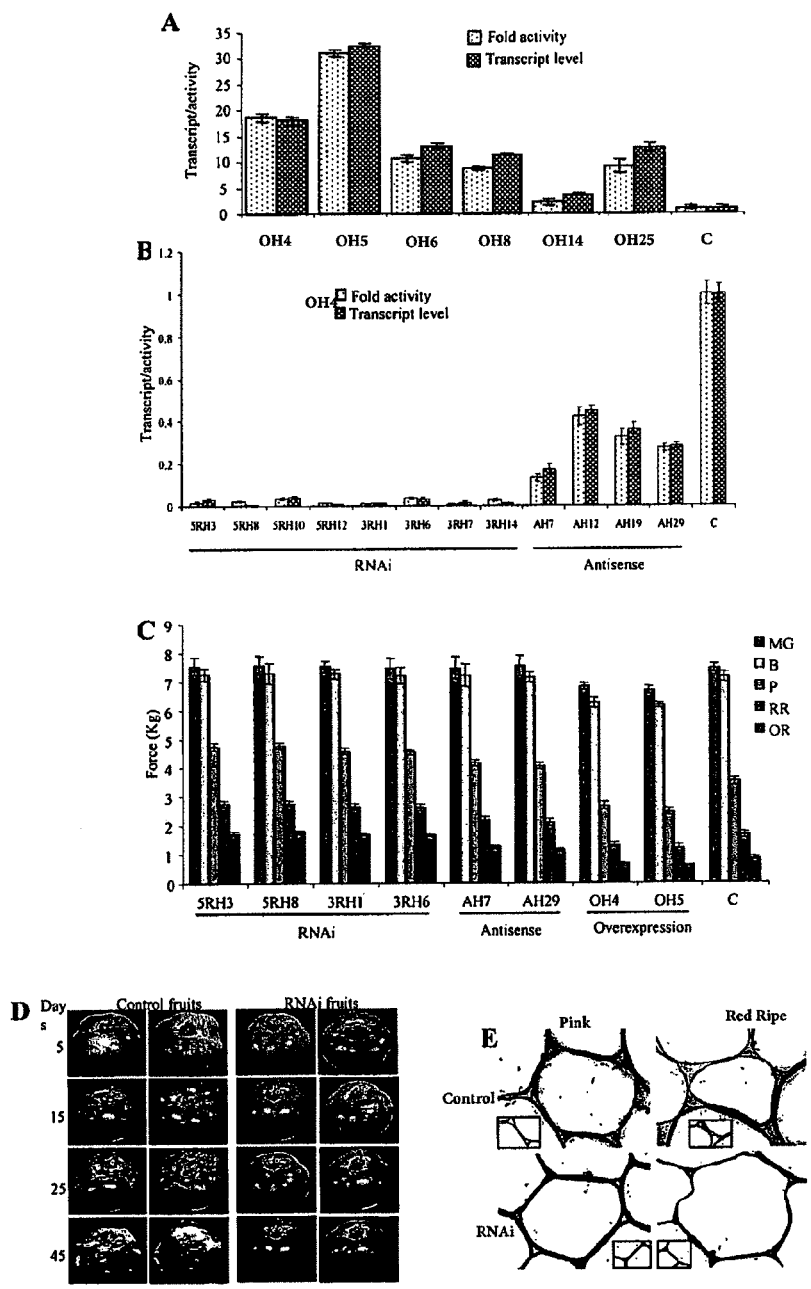

These binary vectors were mobilized to *Agrobacterium tumefaciens* strain EHA 105 through electroporation. Transformed *Agrobacterium* was then grown up to mid log phase and used for plant transformation. Cotyledons of 14 days old tomato seedlings were co-cultivated with *Agrobacterium* and regenerated to through tissue culture techniques. Expression of SlHEX1 gene and β-D-N-acetylhexosaminidase activity was increased up to 32 fold in overexpression lines (FIG. 5A). The gene expression and enzyme activity was suppressed up to 99% in RNAi lines, whereas in case of antisense lines the suppression was in the range of 55%-83% (FIG. 5B). SlHEX1 transgenic fruits undergo essentially normal climacteric ripening, with all the organoleptic characteristics and quality properties that are essential for commercialization. Firmness of the transgenic tomato fruits were measured at different stages of ripening and compared to control fruits (FIG. 5C). Fruit firmness of RNAi and antisense lines was similar to wild type at matured green and breaker stages but it increased from ~1.4 times at pink stage to ~2 times at over ripe stage in RNAi lines and ~1.2 to 1.5 times in antisense lines. Transgenic SlHEX1 constitutive overexpression resulted in enhancement of fruit softening even at matured green stage. The fruits were ~10% and ~30% softer than wild type at matured green and pink stage, respectively. Overexpression and suppression of SlHEX1 in transgenic plants had no effect on vegetative growth, flowering and fruit development, days to maturity and yield.

In addition to compression analysis, the loss of fruit firmness during ripening and consequent spoilage of fruit could be determined qualitatively by seeing the degree of wrinkling of fruit skin. For this, wild type and transgenic fruits, stored at 22-24° C. in 55-60% relative humidity, were examined to see visible signs of fruit softening and photographed at 10-15 days intervals. Although ripening was normal in both wild type and RNAi fruits under these post-harvest storage conditions, the wild type fruits started deteriorating fast after 13-15 days of harvest in comparison to RNAi fruits which showed no signs of softening up to 45 days of harvest (FIG. 5D). We further investigated cell wall changes during ripening of transgenic fruits which revealed reduced cell separation and compact cell wall in RNAi fruits as compared to wild type (FIG. 5E).

In capsicum using similar approach we have transiently silenced the expression of CaHEXO1 which resulted delayed fruit softening compared to control.

In addition to tomato and capsicum, the present invention encompasses producing transgenic plant having delayed fruit softening wherein the plant is selected from a group consisting of tomato, capsicum, mango, banana, papaya, citrus, pineapple, guava, avocado, strawberry, apple, pomegranate and other plants.

One embodiment of the present invention is to provide an isolated polynucleotide coding for a polypeptide having β-D-N-acetylhexosaminidase activity, wherein the nucleotide sequence of said polynucleotide is selected from the group consisting of
 a. a nucleotide sequence coding for a polypeptide having 90% identity with an amino acid sequence as set forth in SEQ ID NO: 3;
 b. a nucleotide sequence coding for a polypeptide having 90% identity with an amino acid sequence as set forth in SEQ ID NO: 5;
 c. a nucleotide sequence coding for a polypeptide having amino acid sequence as set forth in SEQ ID NO: 3;
 d. a nucleotide sequence coding for a polypeptide having amino acid sequence as set forth in SEQ ID NO: 5;
 e. a nucleotide sequence complementary to the nucleotide sequence of (a), (b), (c) or (d);
 f. a nucleotide sequence as set forth in SEQ ID NO: 1;
 g. a nucleotide sequence as set forth in SEQ ID NO: 2;
 h. a nucleotide sequence as set forth in SEQ ID NO: 4; and
 i. a nucleotide sequence complementary to the nucleotide sequence of (f), (g) or (h).

Yet another embodiment of the present invention provides the polynucleotide sequence from tomato, wherein the polynucleotide codes for the polypeptide having the β-D-N-acetylhexosaminidase activity.

Yet another embodiment of the present invention provides the polynucleotide sequence from capsicum, wherein the polynucleotide codes for the polypeptide having the β-D-N-acetylhexosaminidase activity.

Still yet another embodiment of the instant invention provides a DNA construct comprising the polynucleotide sequence coding for the polypeptide having the β-D-N-acetylhexosaminidase activity, wherein the polynucleotide sequence is operably linked to a promoter sequence.

Yet another embodiment of the instant invention provides a DNA construct comprising the part of polynucleotide sequence coding for the polypeptide having the β-D-N-acetylhexosaminidase activity, wherein the nucleotide sequence of the polynucleotide sequence is as set forth in SEQ ID NO: 1, wherein the polynucleotide sequence is operably linked to a promoter sequence, wherein the polynucleotide sequence is in sense and antisense orientation separated by an intron.

Still yet another embodiment of the instant invention provides a DNA construct comprising the part of polynucleotide sequence coding for the polypeptide having the β-D-N-acetylhexosaminidase activity, wherein the nucleotide sequence of the polynucleotide sequence is as set forth in SEQ ID NO: 2, wherein the polynucleotide sequence is operably linked to a promoter sequence, wherein the polynucleotide sequence is in sense and antisense orientation separated by an intron.

Still yet another embodiment of the instant invention provides a DNA construct comprising the part of polynucleotide sequence coding for the polypeptide having the β-D-N-acetylhexosaminidase activity, wherein the nucleotide sequence of the polynucleotide sequence is as set forth in SEQ ID NO 4, wherein the polynucleotide sequence is operably linked to a promoter sequence, wherein the polynucleotide sequence is in sense and antisense orientation separated by an intron.

In further embodiment, the instant invention provides a recombinant vector comprising the DNA construct disclosed in the invention.

Still yet another embodiment of the instant invention provides a recombinant vector comprising the part of polynucleotide sequence coding for the polypeptide having the β-D-N-acetylhexosaminidase activity, wherein the nucleotide sequence of the polynucleotide sequence is as set forth in SEQ ID NO: 1, wherein the polynucleotide sequence is operably linked to a promoter sequence, wherein the polynucleotide sequence is in sense and antisense orientation separated by an intron.

Still yet another embodiment of the instant invention provides a recombinant vector comprising the part of the polynucleotide sequence coding for the polypeptide having the β-D-N-acetylhexosaminidase activity, wherein the nucleotide sequence of the polynucleotide sequence is as set forth in SEQ ID NO: 2, wherein the polynucleotide sequence is operably linked to a promoter sequence, wherein the polynucleotide sequence is in sense and antisense orientation separated by an intron.

Still yet another embodiment of the instant invention provides a recombinant vector comprising part of the polynucleotide sequence coding for the polypeptide having the β-D-N-acetylhexosaminidase activity, wherein the nucleotide sequence of the polynucleotide sequence is as set forth in SEQ ID NO: 4, wherein the polynucleotide sequence is operably linked to a promoter sequence, wherein the polynucleotide sequence is in sense and antisense orientation separated by an intron.

Yet another embodiment of the present invention relates to a recombinant host cell comprising the recombinant vector disclosed in the invention.

Yet another embodiment of the present invention relates to a recombinant host cell comprising the polynucleotide sequence coding for the polypeptide having the β-D-N-acetylhexosaminidase activity, wherein the nucleotide sequence of the polynucleotide sequence is selected from a group consisting of SEQ ID NO: 1, SEQ ID NO: 2 and SEQ ID NO: 4.

One embodiment of the present invention relates to the host cell of the invention, wherein the host cell is selected from the group consisting of *Agrobacterium, E. coli* and yeast.

In one embodiment, the instant invention provides a process for delaying fruit softening in plant; said method comprising transforming a plant cell, tissue or any part thereof with the recombinant vector of the present invention, wherein said vector comprises the part of the polynucleotide sequence of SlHEX1 or CaHEXO1 is in sense and antisense direction separated by an intron.

In one embodiment, the instant invention provides a process for delaying fruit softening in plant; said method comprising transforming a plant cell, tissue or any part thereof with the recombinant vector of the present invention, wherein said vector comprises the polynucleotide sequence SlHEX1 or CaHEXO1 is in antisense direction.

In another embodiment, the present invention provides a process for early fruit softening in plant; said method comprising transforming a plant cell, tissue or any part thereof with the recombinant vector of the present invention, wherein said vector comprises the polynucleotide sequence SlHEX1 or CaHEXO1 is in sense direction that codes for a polypeptide having β-D-N-acetylhexosaminidase activity.

One embodiment of the present invention relates to a transgenic plant produced by the process disclosed in the instant invention, wherein expression of β-D-N-acetylhexosaminidase in said plant is modulated to effect fruit softening, wherein the plant is selected from the group consisting of tomato, capsicum and papaya etc.

One embodiment of the present invention relates to a transgenic plant produced by the method disclosed in the instant invention, wherein expression of β-D-N-acetylhexosaminidase in said plant is modulated to effect fruit softening, wherein the plant is tomato.

One embodiment of the present invention relates to a transiently transformed plant produced by the method disclosed in the instant invention, wherein expression of β-D-N-acetylhexosaminidase in said plant is modulated to effect fruit softening, wherein the plant is capsicum.

One embodiment of the present invention relates to seed or progeny of the transgenic plant produced by the method disclosed in the instant invention, wherein expression of β-D-N-acetylhexosaminidase in said plant is modulated to effect fruit softening.

In one embodiment of the present invention there is provided an isolated polynucleotide coding for a polypeptide having hexosaminidase activity, wherein the nucleotide sequence of said polynucleotide encodes a polypeptide having at least about 88% identity with an amino acid sequence as set forth in SEQ ID NO: 3 or SEQ ID NO: 5.

In another embodiment of the present invention there is provided an isolated polynucleotide coding for a polypeptide having hexosaminidase activity, wherein the nucleotide sequence of said polynucleotide encodes a polypeptide having at least about 90% identity with an amino acid sequence as set forth in SEQ ID NO: 3 or SEQ ID NO: 5.

Another embodiment of the present invention provides an RNAi constructs comprising at least 20 contiguous nucleotides from the polynucleotide encoding a polypeptide having hexosaminidase activity are selected in such a way that these nucleotides form only hairpin structure and do not form the secondary loop within its length, wherein the nucleotide sequence of said polynucleotide encodes a polypeptide having at least about 85% identity with an amino acid sequence as set forth in SEQ ID NO: 3 or SEQ ID NO: 5.

Another embodiment of the present invention provides an RNAi constructs comprising at least 20 contiguous nucleotides from the polynucleotide encoding a polypeptide having hexosaminidase activity are selected in such a way that these nucleotides form only hairpin structure and do not form the secondary loop within its length, wherein the nucleotide sequence of said polynucleotide is as set forth in SEQ ID NO: 1, SEQ ID NO: 2 or SEQ ID NO: 4.

The RNAi constructs disclosed in the present invention form hairpin structure after transcription in the plant.

The RNAi constructs disclosed in the present invention is a hairpin nucleic acid.

The RNAi construct disclosed in the present invention form hairpin structure after transcription in the plant, and does not form the secondary loop structure.

Another embodiment provides an RNAi constructs comprising the polynucleotide sequence as disclosed in the present invention form hairpin structure after transcription in the plant.

In one embodiment of the present invention there is provided an isolated polynucleotide encoding a polypeptide having hexosaminidase activity, wherein the nucleotide sequence of the polynucleotide encodes a polypeptide having at least about 85% identity with an amino acid sequence as set forth in SEQ ID NO: 3 or SEQ ID NO: 5.

In another embodiment of the present invention there is provided a polynucleotide encoding a polypeptide having hexosaminidase activity, wherein the polynucleotide encodes a polypeptide having amino acid sequence as set forth in SEQ ID NO: 3 or SEQ ID NO: 5.

In another embodiment of the present invention there is provided a polynucleotide encoding a polypeptide having hexosaminidase activity, wherein the nucleotide sequence of the polynucleotide is as set forth in SEQ ID NO: 1, SEQ ID NO: 2 or SEQ ID NO: 4.

In another embodiment of the present invention there is provided a polypeptide having amino acid sequence as set forth in SEQ ID NO: 3 or SEQ ID NO: 5.

In another embodiment of the present invention there is provided a DNA construct comprising the polynucleotide encoding a polypeptide having hexosaminidase activity, wherein the nucleotide sequence of the polynucleotide encodes a polypeptide having at least about 85% identity with an amino acid sequence as set forth in SEQ ID NO: 3 or SEQ ID NO: 5, wherein the polynucleotide is operably linked to a promoter sequence.

In another embodiment of the present invention there is provided a DNA construct comprising the polynucleotide encoding a polypeptide having hexosaminidase activity, wherein the polynucleotide encodes a polypeptide having amino acid sequence as set forth in SEQ ID NO: 3 or SEQ ID NO: 5, wherein the polynucleotide is operably linked to a promoter sequence.

In another embodiment of the present invention there is provided a DNA construct comprising a polypeptide having hexosaminidase activity, wherein the nucleotide sequence of the polynucleotide is as set forth in SEQ ID NO: 1, SEQ ID NO: 2 or SEQ ID NO: 4, wherein the polynucleotide is operably linked to a promoter sequence.

In another embodiment of the present invention there is provided a DNA construct comprising the polynucleotide encoding a polypeptide having hexosaminidase activity, wherein the nucleotide sequence of the polynucleotide encodes a polypeptide having at least about 85% identity with an amino acid sequence as set forth in SEQ ID NO: 3 or SEQ ID NO: 5, wherein the polynucleotide is operably linked to a promoter sequence, wherein the polynucleotide sequence is in sense orientation.

In another embodiment of the present invention there is provided a DNA construct comprising the polynucleotide encoding a polypeptide having hexosaminidase activity, wherein the polynucleotide encodes a polypeptide having amino acid sequence as set forth in SEQ ID NO: 3 or SEQ ID NO: 5, wherein the polynucleotide is operably linked to a promoter sequence, wherein the polynucleotide sequence is in sense orientation.

In another embodiment of the present invention there is provided a DNA construct comprising a polypeptide having hexosaminidase activity, wherein the nucleotide sequence of the polynucleotide is as set forth in SEQ ID NO: 1, SEQ ID NO: 2 or SEQ ID NO: 4, wherein the polynucleotide is operably linked to a promoter sequence, wherein the polynucleotide sequence is in sense orientation.

In another embodiment of the present invention there is provided a DNA construct comprising the polynucleotide encoding a polypeptide having hexosaminidase activity, wherein the nucleotide sequence of the polynucleotide encodes a polypeptide having at least about 85% identity with an amino acid sequence as set forth in SEQ ID NO: 3 or SEQ ID NO: 5, wherein the polynucleotide is operably linked to a promoter sequence, wherein the polynucleotide sequence is in anti-sense orientation.

In another embodiment of the present invention there is provided a DNA construct comprising the polynucleotide encoding a polypeptide having hexosaminidase activity, wherein the polynucleotide encodes a polypeptide having amino acid sequence as set forth in SEQ ID NO: 3 or SEQ ID NO: 5, wherein the polynucleotide is operably linked to a promoter sequence, wherein the polynucleotide sequence is in anti-sense orientation.

In another embodiment of the present invention there is provided a DNA construct comprising a polypeptide having hexosaminidase activity, wherein the nucleotide sequence of the polynucleotide is as set forth in SEQ ID NO: 1, SEQ ID NO: 2 or SEQ ID NO: 4, wherein the polynucleotide is operably linked to a promoter sequence, wherein the polynucleotide sequence is in anti-sense orientation.

In another embodiment of the present invention there is provided an RNAi construct for suppressing expression of hexosaminidase in a transgenic plant, the construct comprising a sense polynucleotide strand comprising at least 20 contiguous nucleotides from the sequence as set forth in SEQ ID NO: 2 or SEQ ID NO: 4, and an antisense polynucleotide strand that hybridizes to said sense polynucleotide strand, wherein the antisense polynucleotide strand and the sense polynucleotide strand form a duplex.

In another embodiment of the present invention there is provided an RNAi construct for suppressing expression of hexosaminidase in a transgenic plant, wherein the RNAi construct is a hairpin nucleic acid.

In another embodiment of the present invention there is provided an RNAi construct for suppressing expression of hexosaminidase in a transgenic plant, the construct comprising a sense polynucleotide strand comprising at least 20 contiguous nucleotides from the sequence as set forth in SEQ ID NO: 2 or SEQ ID NO: 4, and an antisense polynucleotide strand that hybridizes to said sense polynucleotide strand, wherein the antisense polynucleotide strand and the sense polynucleotide strand form a duplex, wherein said sense strand comprises 100 to 600 nucleotides.

In another embodiment of the present invention there is provided a recombinant vector comprising the DNA construct as disclosed in the present invention.

In another embodiment of the present invention there is provided a recombinant host cell comprising the recombinant vector as disclosed in the present invention.

In another embodiment of the present invention there is provided host cell selected from the group consisting of *Agrobacterium*, *E. coli* and yeast.

In another embodiment of the present invention there is provided a process for delaying fruit softening in plant, the process comprising transforming a plant cell, tissue or any part thereof with the recombinant vector comprising the polynucleotide encoding a polypeptide having hexosaminidase activity, wherein the nucleotide sequence of the polynucleotide encodes a polypeptide having at least about 85% identity with an amino acid sequence as set forth in SEQ ID NO: 3 or SEQ ID NO: 5, wherein the polynucleotide is in antisense orientation.

In another embodiment of the present invention there is provided a process for delaying fruit softening in plant, the process comprising transforming a plant cell, tissue or any part thereof with the recombinant vector comprising the polynucleotide encoding a polypeptide having hexosaminidase activity, wherein the nucleotide sequence of the polynucleotide selected from the group consisting of SEQ ID NO: 1, SEQ ID NO: 2 and SEQ ID NO: 4.

In another embodiment of the present invention there is provided a process for delaying fruit softening in plant, the process comprising decreasing the level of hexosaminidase in transgenic plant compared to its level in non-transgenic plant by expression of an RNA interference (RNAi) construct comprising at least a fragment of at least 20 contiguous nucleotides of the polynucleotide encoding a polypeptide having hexosaminidase activity, wherein the nucleotide sequence of said polynucleotide encodes a polypeptide having at least about 85% identity with an amino acid sequence as set forth in SEQ ID NO: 3 or SEQ ID NO: 5; and screening the resulting plants for reduced level of hexosaminidase relative to said non-transgenic plant.

In another embodiment of the present invention there is provided a process for delaying fruit softening in plant, the process comprising decreasing the level of hexosaminidase in transgenic plant compared to its level in non-transgenic plant by expression of an RNA interference (RNAi) construct comprising at least a fragment of at least 20 contiguous nucleotides of the polynucleotide encoding a polypeptide having hexosaminidase activity, wherein the nucleotide sequence of the polynucleotide is selected from the group consisting of SEQ ID NO: 1, SEQ ID NO: 2 and SEQ ID NO: 4.

In another embodiment of the present invention there is provided a process for delaying fruit softening in plant, the process comprising decreasing the level of hexosaminidase in transgenic plant compared to its level in non-transgenic plant by expression of an RNA interference (RNAi) construct comprising a sense polynucleotide strand comprising at least 20 contiguous nucleotides from the sequence as set forth in SEQ ID NO: 2 or SEQ ID NO: 4, and an antisense polynucleotide strand that hybridizes to the sense polynucleotide strand, wherein the antisense polynucleotide strand and the sense polynucleotide strand form a duplex; and screening the resulting plants for reduced level of hexosaminidase relative to said non-transgenic plant.

In another embodiment of the present invention there is provided a process for delaying fruit softening in plant using the RNAI constructs, wherein the RNAi construct is a hairpin nucleic acid.

In another embodiment of the present invention there is provided a transgenic plant produced by the process as disclose in the present invention, wherein expression of the hexosaminidase in the plant is controlled to delay fruit softening.

The transgenic plant disclosed in the present invention encompasses tomato, capsicum, papaya, mango, banana, peach, pear, citrus, pineapple, guava, avocado, strawberry, apple and pomegranate.

The transgenic plant as disclosed in the present invention is tomato or capsicum.

In another embodiment of the present invention there is provided a transgenic seed or progeny of the transgenic plant as disclosed in the present invention.

EXAMPLE

It should be understood that the following examples described herein are for illustrative purposes only and that various modifications or changes in light will be suggested to persons skilled in the art and are to be included within the spirit and purview of this application and the scope of the appended claims.

Example 1

Enzyme Assay and Purification of β-D-N-acetylhexosaminidase from Tomato and Capsicum Tomato and capsicum seeds were germinated in pre-sterilized soil and 15 days old seedlings were transplanted to the greenhouse with 25/23° C. temperature, 70% humidity and 14/10 hr light/dark regime. Flowers were tagged at anthesis and fruits were harvested at different stages of ripening.

Enzyme reaction was done using pNP-GlcNAc (0.4 mM) in 10 mM Tris-Cl, pH 6.0 at 37° C. for 15 min and reaction was stopped by adding 20 mM $Na_2CO_3$. The colour thus developed was recorded at 405 nm and the amount of pNP released was determined using a standard curve.

The frozen fruit pericarp was powdered in liquid nitrogen and suspended in one fourth volume of extraction buffer (100 mM Tris-Cl, pH 7.0 with 0.25 M NaCl and 1 mM PMSF) and extracted overnight at 4° C. After passing through four layers of cheesecloth, the extract was centrifuged at 10,000 g to settle down all the debris. The supernatant thus obtained was subjected to 30-80% ammonium sulphate precipitation. The pellet obtained after the precipitation was reconstituted and dialyzed overnight against 25 mM Tris-Cl, pH 7.0 with one change. The sample was then chromatographed on DEAE Sepharose pH 7.0 and eluted with increasing gradient of NaCl. The enzyme eluted at 120 mM salt concentration. The samples containing the activity were pooled and subjected to affinity chromatography on ConA sepharose column and eluted with increasing gradient of α-D-methylmannopyranoside. The enzyme eluted at 100 mM concentration, pooled and concentrated by 0-90% ammonium sulphate saturation. The pellet thus obtained was dissolved in 25 mM Tris-Cl, pH 7.0 and directly loaded on the gel filtration column of Sephadex G100. Fractions were collected after the void volume, assayed for enzyme activity and resolved on 12.5% SDS-PAGE. The enzyme rich fractions were concentrated using CentriconYM30 (Millipore) and stored at 4° C.

Example 2

2DE, SDS-PAGE, LC-MS/MS and Western Blotting

Purified protein was diluted in dilution buffer (200 mM Tris-Cl pH 8.5, 40% glycerol, 8% SDS, 0.4 mM PMSF and 50 mM DTT), boiled for 5 min and precipitated with 9 volumes of 100% chilled acetone. Electrofocusing was performed using IPGphor system (Amersham biosciences) at 20° C. for 40,000 Vhr after passive rehydration of 13 cm long immobiline dry strip (pH 4.0-7.0) for 12 hr with 20 μg of purified protein sample in 250 μl 2DE rehydration buffer (9 M urea, 4% chaps, 2% thiourea, 20 mM DTT, 0.8% IPG buffer and trace amount of bromophenol blue). The focused strips were subjected to reduction with 1% (w/v) DTT in 10 ml of equilibration buffer (50 mM Tris-Cl pH 8.8, 6 M urea, 30% glycerol and 2% SDS) followed by alkylation with 2.5% (w/v) iodoacetamide in the same buffer. The strips were then loaded on top of 12.5% polyacrylamide gels for second dimensional separation on SDS-PAGE. The electrophoresed proteins stained with coomassie blue stain and gel images were digitized with a FluorS imaging system (Bio-Rad, CA). Experimental molecular mass and pI were calculated from digitized 2DE images using standard molecular mass marker proteins. The spots were cut from the gel and analyzed by electrospray ion trap time-of-flight mass spectrometry (LC-MS/MS) (Q-Star Pulsar i, Applied Biosystems). The spectra were analyzed by Mascot sequence matching software against the Viridiplantae (green plants) database.

For western blot analysis 50 μg of the protein, quantified by Bio-Rad protein assay kit and resolved on 12.5% SDS-PAGE was electrotransferred to Hybond-C (Amersham biosciences) membrane at constant current of 150 mA for 2-3 hours. Non specific sites on the membrane were blocked by Blotto in TBS for 1 hr and incubated with the primary antibody (1:2500) overnight at 4° C. Immunodetection was carried out with horseradish peroxidase conjugated anti-rabbit antiserum as secondary antibody for 1 hr and exposing the blot to chemiluminescence substrate (Pierce Biotechnology).

SDA-PAGE analysis of the purified protein reveled a single protein band of 80 kD and native molecular weight of the protein was found to be 300 kD. On 2DE gel purified protein separated into different spots of 80 kD which were found to be representative of β-D-N-acetylhexosaminidase as confirmed by LC-MS/Ms analysis.

Example 3

High Performance Anion Exchange Chromatography

The standard sugar (GlcNAc, Sigma) was prepared in deionized water and injected at a concentration of 100 nmoles before and after the analysis of sample. An HPAE-PAD system (Dionex DX 500 BioLC) equipped with a gradient pump (GP 40), an anion exchange column (Carbopac PA-1, 4×250 mm), an eluant degas module (EDM-2) for pressurizing the eluants with argon was used for the analysis of monosaccharide. The separated monosaccharide was detected by an ED 40 detector equipped with a gold electrode and an Ag/AgCl reference electrode. The resulting chromatographic data was integrated and plotted using a PC based oracle 2 data acquisition system (Indtech Analytical, Bombay). 10 μg of N-glycan substrates were incubated at 37° C. for 12 hr with 0.5 μg of purified protein in a 100 μl reaction mixture. Then the sample was filtered through PVDF membrane to remove the protein and 10 μl of the filtered sample was loaded on to the column.

The tomato enzyme was able to cleave terminal GlcNAc residue from different N-glycans, thus confirming its N-glycan processing ability.

Example 4

Cloning of Tomato and Capsicum β-D-N-acetylhexosaminidases and Sequence Analysis Degenerate gene specific oligonucleotides were designed based on the peptide tags obtained from mass spectrometry (LC-MS/MS) analysis and motifs identified from multiple sequence alignment and were used for rapid amplification of cDNA ends (RACE). Total RNA was isolated from pericarp of pink stage tomato fruit and reverse transcribed to generate cDNA using polyA tail specific oligonucleotide (RACE adapter primer). A gene specific degenerate primer corresponding to the peptide KLNVLHWH (5' AARYTIAATGT-TYTICAYTGGCA 3'-SEQ ID NO: 7, R is A/G, Y is C/T and I is inosine) and a nested primer derived from RACE adapter primer were able to amplify DNA fragment which was cloned into pGEM-T Easy vector (Promega) and sequenced. Analysis of the derived sequences by blastx identified as partial sequence of SlHEX1 of glycosyl hydrolase family 20 (CaZy family). Further, RACE PCR (Invitrogen) was performed to determine the 5' end sequence of the gene. Using similar approached, capsicum CaHEXO1 was cloned. Protein sequences were deduced by back translation. Related protein sequences from other species were taken and ClustalW and phylogenic analysis (MEGA4) were performed.

Tomato SlHEX1 (1876 bp) was cloned into pGEM-T Easy vector and the recombinant vector was named as pGHT. Similarly capsicum CaHEXO1 (1725 bp) was cloned into pGEM-T Easy vector and the recombinant vector was named as pGHC.

Example 5

Subcellular Localization

To generate C-terminal GFP fusion protein, coding sequence lacking the stop codon were PCR amplified using attB appended primers (5' GGGGACAAGTTTGTA-CAAAAAAGCAGGCTATGAGAGGAGAGAAAACAT TCTCC 3'-SEQ ID NO: 9 and 5' GGGACCACTTTGTA-CAAGAAAGCTGGGTGCTAGTAAATGAATGACCTGT GTTAC 3'-SEQ ID NO: 10). attB flanked PCR product was then cloned into entry vector pDONR221 (Invitrogen) by performing a BP recombination reaction. Further LR recombination reaction was carried out between entry clone and Gateway expression vector pK7FWG2, 0. This recombinant binary vector was used for Agrobacterium mediated transient expression of fusion protein in tomato fruit. Agroinjected fruit pericarp was mounted on to the cryostat (Lieca CM1510S) and frozen. Then 10-15 μm slices were cut and taken on the slides to view under fluorescence microscope.

This confirms that β-D-N-acetylhexosaminidase is localized in cell wall.

Example 6

Agrobacterium Based Transient Transformation

Agroinjection was done as described previously (Orzaez D F, Mirabel S, Wieland W H and Granell A (2006) Plant Physiol 140: 3-11) with few modifications. For agroinjection Agrobacterium pre-cultures (3 mL) were grown for 48 hrs form individual colonies at 28° C. in YEP (Yeast extract 1%, peptone 1% and NaCl 0.5%) media with antibiotics. This was transferred to 50 mL induction medium (0.5% beef extract, 0.1% yeast extract, 0.5% Peptone, 0.5% Sucrose, 2 mM $MgSO_4$, 20 mM acetosyringone, 10 mM MES, pH 5.6) with antibiotics and was grown overnight. Next day the culture recovered by centrifugation when the OD reached 1 and resuspended in infiltration medium (10 mM $MgCl_2$, 10 mM MES, 200 mM acetosyringone, pH 5.6) and incubated at room temperature with gentle agitation for 4 hr. 1 mL syringe with 0.5-mm needle was used for agroinjection. Needle was introduced 1 to 2 mm in depth into the fruit pericarp near the stylar apex, and infiltration solution was gently injected in the fruit. Maximum of 500 mL solution was able to be injected. Beyond breaker stage fruits were unfit for injection.

Example 7

RNA Isolation and Quantitative Real Time Reverse Transcriptase PCR (qRT PCR)

RNA was isolated according to LiCl method and quantified using nanodrop (ND 100). Total RNA (5 μg) was reverse transcribed using superscript II (Invitrogen) and diluted five times before using in the qRT PCR reaction. qRT PCR was performed using One Step Real Time RT PCR (Applied Biosystems) with cyber green. The oligonucleotide primers used in the amplification are RTH1F-5' TATGTTCTGG TGGC-CCG 3' (SEQ ID NO: 11) and RTH1R-5' TCTGCTCCTC-CGTGAAAG 3' (SEQ ID NO: 12) for SlHEX1 target amplification and RTTAL-5' TTATCACCATT GGTGCTGAG 3' (SEQ ID NO: 13) and RTTAR-5' CGATGTTTCCATAC AGATCCTT 3' (SEQ ID NO: 14) for endogenous control actin. Relative gene expression was analyzed using $2^{-\Delta\Delta Ct}$ method.

Example 8

Small RNA Isolation and Northern Blotting

Total RNA was enriched for small molecular weight RNA. The RNA after the precipitation with LiCl, was washed with 70% ethanol and the pellet was air dried. The pellet was then dissolved in 1 ml of DEPC water and heated for 65° C. for 5 min, and then placed on ice for 2 min. To precipitate the high molecular weight RNA, polyethylene glycol (molecular weight 8000) and NaCl was added to a final concentration of 5% and 0.5 M, respectively. After 30 minutes of incubation on ice, the RNA was centrifuged at 13,000 rpm for 30 min. The supernatant was precipitated with 3 volumes of ethanol and ⅒ volume of 3M Sodium acetate (pH 5.2) and the tube was placed in −20° C. overnight. Next day the low molecular weight RNA was recovered by centrifugation at 13,000 rpm for 10 min. The pellet was dried and dissolved in 50 µl of DEPC water. Small molecular weight RNA was resolved on 15% urea PAGE containing 0.5×TBE for 4-5 hr at 70 V. Then the gel was electrotransferred to nylon membrane using 0.5× TBE for 1 hr at 100V constant. The nylon membrane was UV cross-linked and pre-hybridized in 50% formamide, 7% SDS and 50 mM $Na_2HPO_4$ and $NaH_2PO_4$, pH 7.2 at 35° C. After 4 hours, the denatured probe was added and hybridization was done for 14-16 hours at 35° C. The blot was washed using 2×SSC and 1% SDS for 2 min at RT, then washed with 0.5×SSC and 0.1% SDS and exposed to the film.

The analysis confirmed the generation of gene specific siRNA in transgenic fruit produced with the RNAi technology.

Example 9

Vectors and Tomato Transformation

To develop RNAi constructs, 500-600 bp 5' or 3' coding region of the gene including UTR was cloned into pHANNI-BAL in sense and antisense orientation separated by an intron. To develop RNAi construct from 5' end sequence of the SlHEX1, PCR amplification was done using primers 5' CCGCTCGAGAAGCAGTGGTATCAACGCA-GAGTACGC 3' (SEQ ID NO-15) or 5'CCGCTCGAG-GAGAAAAAAATGAGAGGAGAGAAAAC 3' (SEQ ID NO-16) and 5' GGAATTCCAGCCTTAACAAGTGATC-GACTCCG 3' (SEQ ID NO: 17) for cloning in sense direction. Similarly, PCR was done for cloning in antisense direction using primers 5' GCTCTAGAAAGCAGTGGTATCAACGCAGAGTACGC 3' (SEQ ID NO: 18) or 5' GCTCTAGAGAGAAAAAAAT-GAGAGGAGAGAAAAC 3' (SEQ ID NO: 19) and 5' CCCAAGCTTCAGCCTTAACAAGTGATCGACTCCG 3' (SEQ ID NO: 20). To develop RNAi construct from 5' end sequence of the SlHEX1, PCR amplification was done using primers 5' CCGCTCGAGCCGTGTGATTGTGTCATCTGC 3' (SEQ ID NO: 21) and 5' GGAATTCGTAAGAAATTC-CCAGATTCATTTGC 3' (SEQ ID NO: 22). Similarly, PCR was done for cloning in antisense direction using primers 5' GCTCTAGACCGTGTGATTGTGTCATCTGC 3' (SEQ ID NO: 23) and 5' CGGGATCCGTAAGAAATTCCCAGAT-TCATTTGC 3' (SEQ ID NO: 24). Finally, the NotI fragment of the construct was cloned into a binary vector, pART27. Antisense and overexpression constructs were prepared in pBI121 vector after removing GUS coding sequence. By PCR amplification, XbaI restriction site was incorporated in the cDNA sequence before start and after stop codon for preparation of overexpression and antisense vectors, respectively. For amplification of sense strand PCR was done using primers 5' GCTCTAGAATGAGAGGAGAGAAAACAT-TCTCC 3' (SEQ ID NO: 25) and 5' TCAGCTAGTAAAT-GAATGAACTG 3' (SEQ ID NO: 26). For cloning in antisense direction PCR was done using primers 5' ATGAGAGGAGAGAAAACATTCTCC 3' (SEQ ID NO: 27) and 5' GCTCTAGAGTAAGAAATTCCCAGAT-TCATTTGC 3' (SEQ ID NO: 28). PCR product was then ligated into XbaI/Ecl136II site of pBI121.

Transgenic tomato plants were generated by *Agrobacterium* mediated transformation of tomato cotyledon leaves. After cutting, explants were placed on MS media (Sigma) containing zeatin (10 µg/ml) as callusing and shooting hormone (shooting media) and kept for one day under tissue culture condition (24° C., 65% relative humidity, 14/10 hr light-dark cycle). After one day these explants were used for transformation. *Agrobacterium* were grown in YEP media for transformation. *Agrobacterium* cells were pellet suspended in liquid MS containing Acetosyringone. The cell suspension were added to explants and co-cultivated. After co-cultivation explants were transferred to MS (shooting media) and kept at 28° C. After two days, explants were transferred to shooting media containing Cefotaxime and maintained at tissue culture condition. Then explants were further transferred to shooting media containing Cefotaxime and Kanamycin. Explants were maintained in this media for two to three and half months with regular change. Shoots (3-4 cm in length) were then transferred to rooting media with hormone IAA (10 µg/ml) and antibiotics (Cefotaxime and Kanamycin) and maintained for 1-2 months. Leaves were collected from rooted plants for DNA extraction (CTAB method) and Polymerase Chain Reaction (PCR) was performed to determine putative transformants. 7-10% frequency of regeneration and transformation was achieved through this *Agrobacterium* mediated gene transfer method. PCR positive plants were transferred to green house after hardening Example 10

Textural Analysis

Fruit firmness was determined using TA-XT Plus (Stable Microsystems, UK). Each fruit was analyzed with 75 mm wide P75 compression plate loading at 1 mm $s^{-1}$. The fruits were compressed to a vertical displacement of 5 mm. Firmness was defined as the response force to a 5 g applied force. The values were subjected to Student's t-test to find the significant difference.

The textural analysis reveled 2 fold increase in the fruit firmness of the transgenic fruit as compared to the non transgenic fruit.

Example 11

ACC Treatment to the Seedlings

Fifteen days old tomato seedlings (Pusa ruby), germinated and grown in MS medium were used for ACC treatment. Seedlings from MS media were transferred to liquid MS containing 0.1 mM ACC and harvested after 30 min, 1 hr, 2 hr, 4 hr, 8 hr, 12 hr and 16 hr of treatment. Seedlings were frozen immediately in liquid nitrogen and RNA was isolated as mentioned above. Further RNA was reverse transcribed to cDNA and used for qRT-PCR. Expression was calculated relative to the control seedlings (0 hr).

This experiment confirms the up-regulation of SlHEX1 gene by ethylene.

Example 12

Staining and Microscopy

Sections were cut in a cryostat microtome (Leica 1050) and were allowed to dry on the poly-1-lysine coated slides. The slides were dipped in aqueous solution of 0.05% toluidine blue (Sigma) in 0.1 M phosphate buffer at pH 6.8 for 2 min. and washed in milliQ water for 2 minutes. The stained sections mounted in milliQ water under a cover slip and photographed at 40× magnification using Nikon 80i epiflouresent/phage contrast/Bright field microscope.

Staining of tomato fruit cell wall followed by microscopy revealed reduced cell separation and compact cell wall in transgenic fruit as compared to non transgenic fruit.

```
Complete genomic sequence of Solanum lycopersicum
β-D-N-acetylhexosaminidase 1 (2510 nts)
                                           SEQ ID NO: 1
ATGAGAGGAGAGAAAACATTCTCCTTCTTTCTTCTATTATTCTTTATC

TTAATTTCACAAACAACAGCCACAAATTACCCAATCAATGTCTGGCCC

AAGCCCACAACATTCCTTTGGCCCAACCCAAAATCCATCTTCCTCTCC

ACAAACTTCACCATCTCCCACCCGTACCACCGGTACCTCACTCCCGCC

GTCGACCGTTACCGCCACCTCATCCTCTCCGAACACCACCGTCCCATC

ATAACTCCCGCTATCAACCTCACTTCATCAATTCCGTTACAAAGCCTT

GTCATCTCCGTCTCCGATGTCACTTCACCACTCGCTCACGGAGTCAAC

GAATCCTACTCTCTCTCCACACCTTCCGACGGCTCCGCCTCCGCCTAC

ATATCTGCGGCGACTGTATGGGGAGCCATGCGAGGGCTGGAGACATTC

TCACAACTCGTGTACGGAAACCCTACCAGAGTTTCCGCCGGCGTGTAT

ATACACGATCTACCGATTTTTACTCACAGAGGTGTGATGTTGGATACT

TCGAGAAATTTCTACGGAGTCGATCACTTGTTAAGGCTGATTAAAGCT

ATGAGTATGAACAAGTTGAATGTTTTTCACTGGCATATAACTGATTCA

CATTCATTTCCGCTTGTGATCCCGTCGGAGCCTGAGCTCGCCGGAAAA

GGAGCGTACAGCAACGAGATGATGTATTCGCCGGCGGACGTGCAGAAG

ATCGTGGAATATGGAATGGAACACGGAGTTAGGGTTTTACCTGAAATT

GACATGCCTGGTAAGTTATGGAATCACGATAAAGTATAATAGAATAAT

GTATGGATAATTTTCGTTTACAATTTCTAGGTAATCCCGAAAAGGAAC

AAGATTGGACTTTTGGAAGTATTATTAATTTATCAGGATATGGGGATC

ATTAATTTATTAATATTAACTTAATGGGACCTTGGTGGATTTTTTGGA

ACTTTTTCTTCTGGCAAATGAAAATGTATATATCTTTTTATACAGGAA

ACCAAAACCTTTAAGCCTGGGTTTGGGAAGGTAGTGTGGGTTTGGGAA

GGTAGTGTGTATGAACCGCTGTTCTTTTGAGTACTCTTCTCGATACGA

ATAAGAGATTATGTTTGATACTTICAGTGAGATGTGAATGAGAGTTTA

GATGGTTGACGATCTCAATCTTGATATTCGGCTCCATTTTTTTATGG

TAGTTCCGTAGGTAGGATTTTGACAATTTTGTTTACATGGTGTGCAAA

GAACTATGAATTTTAGATTATCTTGTAAACCAGCTTGATAAAGGGTAA

TGGAAGGGACAGTCTTGTCTTTGGTACCACTGAAAGTGCGATAGTCCT

TATTACTGCAATTGATATTTTGTTAAAATCCAAATGAGAGGCAAATTG

CTATATCCTCCACAGAAGAAGGTTATATCATGTTGTAAAGCACGTCAA

AATTTCTTTTGTTAAACATAGAATCACATATGGATATCTTTGTGGACA

TAGGAACAAAGGTAAGTGTATTGGTAACACTATTAAATGTCTGAAGTT

TGTCCCATTTTGCAAATATTGCAGCACATACAGGATCCTGGGCTGAAG

CTTACCCTGAGATAGTCACTTGTGCAAATATGTTCTGGTGGCCCGCTG

GAAGTAGTCCAGCTCTTGCAGCTGAACCAGGCACTGGCCAACTGAACC

CATCGATTCCCAAGACCTATGAAGTAGTCAAGAATGTCATCCAGGGCA

CTATCGCCATGTTTCCGGATTCACTCTTTCACGGAGGAGCAGATGAGA

TCAATTCAGACTGTTGGAATACTGATCTATCAGTCCAAAAGTTTGTTG

CTAGCAATGGAACTCTCAGTCAGCTACTAGAGAAGTTTATCAATAATA

CCTTACCTGAAATCCTCTCACTCAATCGTACGGTGGTCTACTGGGAGG

ATGTTATATTGAGTGGTAATGTGAAAGTGAATCCATCTCTGCTTCCTC

CACAGAATGTTATTATGCAAACTTGGAATAATGGACCAAACAATACAA

AGCAGCTTGTCACTTCTGGCTACCGTGTGATTGTGTCATCTGCAGATT

ACTATTACTTGGATTGTGGCCATGGAAGCTTCGTTGGGAATGACAGCC

GCTATGATCAGCCACCAGGTACTGACCAAGGCAATGGCGGATCATGGT

GTGGGCCTTTCAAGACGTGGGAAACCATTTACAACTATGATATAACCT

ACGGCCTAACTGATGAGGAGGCTCCATTGGTAATTGGAGGGGAAGTAG

CATTATGGTCCGAACAAGCTGATTCAACTGTTATGGACTCAAGGATTT

GGCCAAGAGCATCAGCAATGGCAGAAGCATTGTGGTCAGGAAATCGTG

ATGAAACAGGAATGAAGAGATATGCAGAGGCTACTGATCGACTGAATG

AATGGAGGTACAGAATGGTTTCTAGGGGAATAGGTGCTGAATCGATTC

AACCACTTTGGTGTCTCAAAAACCCAGGCATGTGTAACACAGTTCATT

CATTTACTAGCTGA

Complete cDNA sequence of Solanum lycopersicum
β-D-N-acetylhexosaminidase 1 (1876 nts)
                                           SEQ ID NO: 2
GAGAAAAAAATGAGAGGAGAGAAAACATTCTCCTTCTTTCTTCTATTA

TTCTTTATCTTAATTTCACAAACAACAGCCACAAATTACCCAATCAAT

GTCTGGCCCAAGCCCACAACATTCCTTTGGCCCAACCCAAAATCCATC

TTCCTCTCCACAAACTTCACCATCTCCCACCCGTACCACCGGTACCTC

ACTCCCGCCGTCGACCGTTACCGCCACCTCATCCTCTCCGAACACCAC
```

-continued

CGTCCCATCATAACTCCCGCTATCAACCTCACTTCATCAATTCCGTTA

CAAAGCCTTGTCATCTCCGTCTCCGATGTCACTTCACCACTCGCTCAC

GGAGTCAACGAATCCTACTCTCTCCACACCTTCCGACGGCTCCGCC

TCCGCCTACATATCTGCGGCGACTGTATGGGGAGCCATGCGAGGGCTG

GAGACATTCTCACAACTCGTGTACGGAAACCCTACCAGAGTTTCCGCC

GGCGTGTATATACGATCTACCGATTTTTACTCACAGAGGTGTGATG

TTGGATACTTCGAGAAATTTCTACGGAGTCGATCACTTGTTAAGGCTG

ATTAAAGCTATGAGTATGAACAAGTTGAATGTTTTTCACTGGCATATA

ACTGATTCACATTCATTTCCGCTTGTGATCCCGTCGGAGCCTGAGCTC

GCCGGAAAGGAGCGTACAGCAACGAGATGATGTATTCGCCGGCGGAC

GTGCAGAAGATCGTGGAATATGGAATGGAACACGGAGTTAGGGTTTA

CCTGAAATTGACATGCCTGCACATACAGGATCCTGGGCTGAAGCTTAC

CCTGAGATAGTCACTTGTGCAAATATGTTCTGGTGGCCCGCTGGAAGT

AGTCCAGCTCTTGCAGCTGAACCAGGCACTGGCCAACTGAACCCATCG

ATTCCCAAGACCTATGAAGTAGTCAAGAATGTCATCCAGGGCACTATC

GCCATGTTTCCGGATTCACTCTTTCACGGAGGAGCAGATGAGATCAAT

TCAGACTGTTGGAATACTGATCTATCAGTCCAAAAGTTTGTTGCTAGC

AATGGAACTCTCAGTCAGCTACTAGAGAAGTTTATCAATAATACCTTA

CCTGAAATCCTCTCACTCAATCGTACGGTGGTCTACTGGGAGGATGTT

ATATTGAGTGGTAATGTGAAAGTAATCCATCTCTGCTTCCTCCACAG

AATGTTATTATGCAAACTTGGAATAATGGACCAAACAATACAAAGCAG

CTTGTCACTTCTGGCTACCGTGTGATTGTGTCATCTGCAGATTACTAT

TACTTGGATTGTGGCCATGGAAGCTTCGTTGGGAATGACAGCCGCTAT

GATCAGCCACCAGGTACTGACCAAGGCAATGCGGATCATGGTGTGGG

CCTTTCAAGACGTGGGAAACCATTTACAACTATGATATAACCTACGGC

CTAACTGATGAGGAGGCTCCATTGGTAATTGGAGGGGAAGTAGCATTA

TGGTCCGAACAAGCTGATTCAACTGTTATGGACTCAAGGATTTGGCCA

AGAGCATCAGCAATGGCAGAAGCATTGTGGTCAGGAAATCGTGATGAA

ACAGGAATGAAGAGATATGCAGAGGCTACTGATCGACTGAATGAATGG

AGGTACAGAATGGTTTCTAGGGGAATAGGTGCTGAATCGATTCAACCA

CTTTGGTGTCTCAAAAACCCAGGCATGTGTAACACAGTTCATTCATTT

ACTAGCTGATCCTTCATCAGTGTCTGTACCAGTCATTTATCTGTATTA

TCTTCTATATTCAGATCCAGTTTTATTATTGTAATGTTACCTTCTATTG

TCACCACATTACCATGATTTTACTAGGCAAATGAATCTGGGAATTTCT

TACA

Amino acids sequence of Solanum lycopersicum
β-D-N-acetylhexosaminidase 1 (575 aa)
SEQ ID NO: 3
MRGEKTFSFFLLLFFILISQTTATNYPINVWPKPTTFLWPNPKSIFLS

TNFTISHPYHRYLTPAVDRYRHLILSEHHRPIITPAINLTSSIPLQSL

VISVSDVTSPLAHGVNESYSLSTPSDGSASAYISAATVWGAMRGLETF

SQLVYGNPTRVSAGVYIHDLPIFTHRGVMLDTSRNFYGVDHLLRLIKA

-continued

MSIVINKLNVFHWHITDSHSFPLVIPSEPELAGKGAYSNEMMYSPADV

QKIVEYGMEHGVRVLPEIDMPAHTGSWAEAYPEIVTCANMFWWPAGSS

PALAAEPGTGQLNPSIPKTYEVVKNVIQGTIAMFPDSLFHGGADEINS

DCWNTDLSVQKFVASNGTLSQLLEKFINNTLPEILSLNRTVVYWEDVI

LSGNVKVNPSLLPPQNVIMQTWNNGPNNTKQLVTSGYRVIVSSADYYY

LDCGHGSFVGNDSRYDQPPGTDQGNGGSWCGPFKTWETIYNYDITYGL

TDEEAPLVIGGEVALWSEQADSTVMDSRIWPRASAMAEALWSGNRDET

GMKRYAEATDRLNEWRYRMVSRGIGAESIQPLWCLKNPGMCNTVHSFT

S

Complete cDNA sequence of Capsicum annuum β-D-N-acetylhexosaminidase1 (1725 nts)
SEQ ID NO: 4
ATGAGAGGAGACACAACATTCCCATTCATTCTTTCACTATTCGTTATC

TTCATTACTCAAACAATAGCTACAAATTACCCAATTAATGTCTGGCCC

AAGCCCACAACATTCAATTGGCCCAACCCAAAAATCCATCTTCCTCTC

CCCAACTTCACCATCTCCCACCCGACCCACCGTTACCTAACTCCCACC

GTTTACCGGTACCGCCGTCTCATCCTCTCCGAGCACTACCGCCACATC

ATCACTCCGTCGATCAACCTGACGTCATCAACTCCGTTACAACACCTC

ATCATCTCCGTCTCCGACGTCACTTCACCGTTATCTCACGGCGTCAAC

GAATCCTACTCTCTCCACGCCTAACGGTTCTTCCGCCGCCTACATA

ACTGCCGGTACCGTATGGGAGCCATGAGAGGACTCGAGACATTCTCA

CAGCTCGTACGGAAACCCTACTCGAGTCGCCGCAGGCGTGTACATA

TCCGATCTGCCGATTTTCACTCACCGTGGTGTGATGTTGGACACTTCG

AGAAACTTCTACGGAGTAGATGATTTGTTGAGGCTTATCAAAGCTATG

AGTATGAACAAGCTGAATGTTTTTCACTGGCACATAACTGATTCACAT

TCGTTTCCGCTTGTGGTTCCATCGGAGCCGGAGCTTGCCGGAAAAGGA

GCATACGGCAATGAGATGATGTACTCGCCGGCGGATGTGGAGAAGATT

GTGGAATTTGGAATGGAACATGGAGTTAGGGTTTACCTGAGATTGAT

ATGCCCGCACATACGGGATCATGGGCTGAAGCTTACCCTGAGATTATC

ACTTGTGCAAATATGTTCTGGTGGCCTGCTGGAAATAGTCCAGCTCTT

GCAGCTGAACCAGGCACTGGTCAACTGAACCCTTTGATTCCCAAAACC

TATGAAGTAGTCAAGAATGTCATCCACGATACCATCGCCATGTTTCCA

GATTCCCTCTTTCACGGGGAGCAGATGAGATCAATTCAGCATGTTGG

AATACTGATCCATCAATCCAAACGTTTGTTGCTAGCAATGGAACTCAG

AGTCAGCTACTCGAAATGTTTATCAATAATACCTTACCTGAAATCCTC

TCACTCAACCGTACTGTGGTCTACTGGGAGGATGTTATATTGAGTGCT

AATGTGAAGGTGGATCCATCTCTGCTTTCGCCACAACATGTTATCATG

CAAACTTGGAATAATGGACCAAGCAATACAAAGCAGCTCGTCACTTCT

GGGTACCGTGTCATTGTGTCATCTGCAGATTACTATTACTTGGATTGT

GGCCATGGGAGTTTCGTTGGAAATGACAGCCGCTATGACCAGCCCCCA

GGTACTGACCAAGGCAATGGTGGATCCTGGTGTGGACCTTTCAAGACC

TGGGAAACCATTTACAACTATGATATAACCTATGGTCTGACTGATAAG

-continued

```
GAGGCTCAATTGGTAATCGGAGGGGAAGTAGCATTATGGTCCGAACAA
GCTGATTCAACTGTTATGGACTCACGAATTTGGCCTAGAGCATCAGCA
ATGGCAGAGACATTGTGGTCAGGGAATTGCGATGAAACAGGAATGAAG
AGATATGCAGAGGCTACTGATCGACTGACTGAATGGAGGTACAGAATG
GTTGCTAGGGGAATAGGTGCTGAACCTATTCAACCACTTTGGTGTGTC
AAAAACTCAGGAATGTGTAACACAGTTCATTCATTTACTAGCTGA
```

Amino acids sequence of Capsicum annuum β-D-N-acetylhexosaminidase 1 (574 aa)

SEQ ID NO: 5

```
MRGDTTFPFILSLFVIFITQTIATNYPINVWPKPTTFNWPNPKIHLPL
PNFTISHPTHRYLTPTVYRYRRLILSEHYRHIITPSINLTSSTPLQHL
IISVSDVTSPLSHGVNESYSLSTPNGSSAAYITAGTVWGAMRGLETFS
QLVYGNPTRVAAGVYISDLPIFTHRGVMLDTSRNFYGVDDLLRLIKAM
SMNKLNVFHWHITDSHSFPLVVPSEPELAGKGAYGNEMMYSPADVEKI
VEFGMEHGVRVLPEIDMPAHTGSWAEAYPEIITCANMFWWPAGNSPAL
AAEPGTGQLNPLIPKTYEVVKNVIHDTIAMFPDSLFHGGADEINSACW
NTDPSIQTFVASNGTQSQLLEMFINNTLPEILSLNRTVVYWEDVILSA
NVKVDPSLLSPQHVIMQTWNNGPSNTKQLVTSGYRVIVSSADYYYLDC
GHGSFVGNDSRYDQPPGTDQGNGGSWCGPFKTWETIYNYDITYGLTDK
EAQLVIGGEVALWSEQADSTVMDSRIWPRASAMAETLWSGNCDETGMK
RYAEATDRLTEWRYRMVARGIGAEPIQPLWCVKNSGMCNTVHSFTS
```

---

What is claimed:

1. A cDNA:
   encoding a polypeptide having β-D-N-acetylhexosaminidase activity, wherein the amino acid sequence of the polypeptide is the amino acid sequence as set forth in SEQ ID NO: 3 or SEQ ID NO: 5.

2. The cDNA as claimed in claim 1, wherein the nucleotide sequence of the polynucleotide is as set forth in SEQ ID NO: 1, SEQ ID NO: 2 or SEQ ID NO: 4.

3. A DNA construct comprising the cDNA as claimed in claim 1, wherein the cDNA is operably linked to a heterologous promoter sequence.

4. The DNA construct as claimed in claim 3, wherein the cDNA is in sense orientation.

5. An RNAi construct for suppressing expression of β-D-N-acetylhexosaminidase in a transgenic plant, said construct comprising as operably linked components:
   (i) a sense polynucleotide strand comprising at least 20 contiguous nucleotides from the sequence as set forth in SEQ ID NO: 2 or SEQ ID NO: 4 operably linked to a heterologous promoter in the sense orientation,
   (ii) a spacer sequence,
   (iii) the polynucleotide strand of (i) in the anti-sense orientation, and
   (iv) a transcription terminator sequence.

6. A recombinant vector comprising the DNA construct as claimed in claim 3.

7. A DNA construct comprising a cDNA encoding a polypeptide having β-D-N-acetylhexosaminidase activity wherein the amino acid sequence of the polypeptide is the amino acid sequence set forth in SEQ ID NO: 5, wherein the cDNA is operably linked to a heterologous promoter.

8. A recombinant host cell comprising the recombinant vector as claimed in claim 6 or 7.

9. The recombinant host cell as claimed in claim 8 is selected from the group consisting of *Agrobacterium*, *E. coli*, and yeast.

10. A process for delaying fruit softening in a plant, said process comprising transforming a plant cell, tissue or any part thereof with the recombinant vector comprising a DNA construct comprising a cDNA encoding a polypeptide having the amino acid sequence as set forth in SEQ ID NO: 3 or SEQ ID NO: 5, operably linked to a heterologous promoter, wherein said cDNA is in the anti-sense orientation, and regenerating a transgenic plant from said transformed cell tissue or part thereof, wherein expression of an endogenous β-D-N-acetylhexosaminidase in said plant is suppressed to delay fruit softening.

11. The process as claimed in claim 10, wherein the nucleotide sequence of the cDNA as set forth in SEQ ID NO: 1, SEQ ID NO: 2 and SEQ ID NO: 4.

12. A process for delaying fruit softening in a plant, said process comprising transforming a plant cell or tissue with a recombinant vector comprising an RNA interference (RNAi) construct comprising (i) a polynucleotide strand of at least 20 contiguous nucleotides selected from SEQ ID NO: 1, SEQ ID NO: 2 and SEQ ID NO: 4 operably linked to a heterologous promoter in the sense orientation, and (ii) the polynucleotide from (i) in the anti-sense orientation, wherein RNA transcribed from said sense and anti-sense strands hybridize to form a hairpin structure, and regenerating a transgenic plant from said transformed cell tissue or part thereof, wherein expression of an endogenous β-D-N-acetylhexosaminidase in said plant is suppressed to delay fruit softening.

13. The process as claimed in claim 12, wherein the nucleotide sequence of the polynucleotide strand operably linked to a heterologous promoter in the sense or anti-sense orientation is selected from the group consisting of SEQ ID NO: 1, SEQ ID NO: 2 and SEQ ID NO: 4.

14. A transgenic plant or a transgenic seed produced by the process as claimed in claim 10 or 12, wherein expression of an endogenous β-D-N-acetylhexosaminidase in said plant is controlled to delay fruit softening.

15. The transgenic plant as claimed in claim 14 wherein the plant is tomato or *capsicum*.

16. The DNA construct as claimed in claim 3, wherein the polynucleotide sequence of the cDNA is set forth in SEQ ID NO: SEQ ID NO: 1, SEQ ID NO: 2 and SEQ ID NO: 4.

17. A recombinant vector comprising the construct as claimed in claim 5.

18. The DNA construct as claimed in claim 7, wherein the cDNA is in the sense or anti-sense orientation.

* * * * *

SEQUENCE LISTING

<160> NUMBER OF SEQ ID NOS: 28

<210> SEQ ID NO 1
<211> LENGTH: 3411
<212> TYPE: DNA
<213> ORGANISM: Solanum lycopersicum

<400> SEQUENCE: 1

```
gagagatttg gggtttatgg tttagtacat tctctttcag tgaacactct cagcaattgt    60
ggaaatgaaa aatatgggga agtttgaaat ttggttcttg attttgatgg tttgtgggtt   120
gtgggtagtg gaagctaagt atatggttta caatacatca cagggaattg tttcagggaa   180
gcttaacgtt catttggttc ctcacactca cgatgatgtt ggctggttga aaacggtcga   240
tcagtactat gttggttcca acaattccat tcaggtggct tgtgttcaaa atgtcttgga   300
ttcattgatt ccagcattat tggctgataa aaacagaaag ttcattttatg ttgaacaggc   360
ttttttccag cgttggtgga ggaatcagag cccgggaatg cagagcacag tcaaacagct   420
cgtcaactcg ggtcaacttg agtccataaa tggaggttgg tgcatgcatg atgaggcagc   480
aacacattat attgacatga tagatcagac aactctaggg cataaataca tcaaacaaca   540
gttcaatgtt actcctagaa ttggctggca aatcgaccct tttgggacat tctgctgttc   600
aggcatacct tctgggagca agggttggat tcgactctct tttctttggg acgcattgac   660
taccaaggac agagaaaaga ggaaaattga aagagccttt gaggtcattt ggaggggttc   720
taagagtctc agttcatcca cgcaaatatt ttcaggtgca ttccctcaga attatgaacc   780
tcccagcaaa ttttactttg aagtgaatga tgataattct cttcctgttc aggatgatgt   840
caacctgttt gactacaatg tccaagagcg ggtcaatgac tttgttgctg ctgctttgtc   900
ccaagccaat atcactcgca caaatcatat aatgtggacc atgggaaccg acttcaagta   960
ccaatatgct catacatggt ttcggaatat ggacaagctc attcactacg taaaccaaga  1020
tggtcgtgtc aatgcttat attcaagccc ttcaatttat actgatgcaa agtatgcttt  1080
ggacgagtca tggcctctca agacggatga ctatttcccg tacgcagacc gtattaatgc  1140
ttattggact ggatacttta caagtaggcc tgctctcaaa ctctatgtta gaatgatgag  1200
tggctattat ttggcagcaa ggcaattaga attctttaaa ggaagaattg agacaggacc  1260
aacaaccgaa atattggctg atgccctagc catcgctcaa catcatgatg ctgtcagtgg  1320
cactccaaag caacatgttg ctgatgatta tgccaaacga ctgttcatag gttacaagca  1380
```

```
ggctgaggat ttagtgtcta attcacttgc ttgtatggtg gaatcagctt cagcatctgg      1440
atgcaagaat cctcagataa atttcaagca gtgcccgttg ttgaatataa gttattgtcc      1500
cccaacagaa gctgatcttg ctccaggcaa aaaattagtg gttgtcgtgt acaatgctct      1560
tgggtggaaa agaacagatg ttgtcagaat ccctgtcgtc aataagaatg tcatcgttga      1620
ggattccact ggaaaagaaa ttgaatcaca gcttcttcca atagttaaag aatcaatagt      1680
aataaggaac tactatgctg cagcatactt tggtgaatcc cctacatcaa gccccaaata      1740
ttggcttgtg tttacagcca ctgttccacc tttgggcttt agctcctatg ttataacaag      1800
tggtaaacaa gcagttgctg cttcaatacc acagacgttc tacaaaactg atggaagtca      1860
aagtgatgca gtagaagtgg ggccggggaa cttgaaactg ttatattctg caaatggggc      1920
aaagtttact caatatttta ataagagaaa ccaggttaga agctctttgg agcaatcatt      1980
cagttattat tctgcagacg atggaagcaa ggatgattat aaagacattc aggcatctgg      2040
agcatatgtg tttcgcccaa acggctcatt ccccatccac cctgagggaa aggtcccagc      2100
taccattcta cgaggtccgc tgctagatga agttcatcaa aatatcaatt catggatata      2160
tcagatcact agagtgtaca aggaaaagga gcacgttgaa gttgagttca ctgttggccc      2220 cataccatt gacaatggaa ttgggaaaga gctggtgact cagattcaaa ctgacatcaa       2280
aagcaacaaa acattctaca cagactctaa tggacgtgat ttccttaaaa gagttcggga      2340
ttatagagct gactgggatc ttcaagtgaa ccaacctgct gctggaaatt attatcctat      2400
caatcttgga cttttcctaa aggacaacaa caacgagttc tcagttttgg ttgatagatc      2460
tgtaggtgga tccagccttg ttgatggcca attggagcta atgcttcacc ggaggttact      2520
caatgatgat ggaagaggtg ttgctgaagc actgaatgaa accgtctgtg ctcttggaaa      2580
atgcatgggc ttgactgtcc aaggcaagta ctatatccgg attgattctc ttggagaggg      2640
agcgaaatgg cggcggtcat ttggacagga gatatattct ccattgcttc tagcttttac      2700
tgagcaggat ggagataaat ttacaaaatt tccagttcca acctttacag ggatggaccc      2760
atcttacagt ctgcctgata atgttgcaat aattacgctt caggagcttg aagatcacac      2820
cgtcctcctg agattggctc atttatacga ggttgatgag gataaggatc tatccaccaa      2880
ggcaagtgta gaattgaaaa gattgttccc aaagaggaag ataaacaaga ttagagagat      2940
gagtttatct gccaaccaag aaagagtaga atggagaag aagagattaa agtggaaagc       3000
agaggctcct agtgatttgc gagacgtggc aagaggggga cctgttgatc ctacaaagct      3060
gatggtagag ctcgccccaa tggaaattcg cacctttgtt attgatctca gccagagcgt      3120
gccagaaggt tggaagtcac atatgtctct atgatagcag tctcctgcag cagtccaatc      3180
caatccgaat cgtcaagacg tcaaaagggt atatgagcag cttgaaacct tcttgggacc      3240
tatttgcctg tgttgatatc accttgagga ggcagcattg agtctcttgt tagaagatgt      3300
gttatccttt ttgtaatgga atgaaaacct ctttgacaga acaataaact tataataata      3360
ataatgatgt tgaagagaga acttccatgt cttagcaaaa aaaaaaaaa a                3411

<210> SEQ ID NO 2
<211> LENGTH: 1876
<212> TYPE: DNA
<213> ORGANISM: Solanum lycopersicum

<400> SEQUENCE: 2
gagaaaaaaa tgagaggaga gaaaacattc tccttctttc ttctattatt ctttatctta        60
```

-continued

| | |
|---|---|
| atttcacaaa caacagccac aaattaccca atcaatgtct ggcccaagcc cacaacattc | 120 |
| ctttggccca acccaaaatc catcttcctc tccacaaact tcaccatctc ccacccgtac | 180 |
| caccggtacc tcactcccgc cgtcgaccgt taccgccacc tcatcctctc cgaacaccac | 240 |
| cgtcccatca taactcccgc tatcaacctc acttcatcaa ttccgttaca aagccttgtc | 300 |
| atctccgtct ccgatgtcac ttcaccactc gctcacggag tcaacgaatc ctactctctc | 360 |
| tccacacctt ccgacggctc cgcctccgcc tacatatctg cggcgactgt atggggagcc | 420 |
| atgcgagggc tggagacatt ctcacaactc gtgtacggaa ccctaccag agtttccgcc | 480 |
| ggcgtgtata tacacgatct accgattttt actcacagag gtgtgatgtt ggatacttcg | 540 |
| agaaatttct acggagtcga tcacttgtta aggctgatta aagctatgag tatgaacaag | 600 |
| ttgaatgttt ttcactggca tataactgat tcacattcat ttccgcttgt gatcccgtcg | 660 |
| gagcctgagc tcgccggaaa aggagcgtac agcaacgaga tgatgtattc gccggcggac | 720 |
| gtgcagaaga tcgtggaata tggaatggaa cacggagtta gggttttacc tgaaattgac | 780 |
| atgcctgcac atacaggatc ctgggctgaa gcttaccctg agatagtcac ttgtgcaaat | 840 |
| atgttctggt ggcccgctgg aagtagtcca gctcttgcag ctgaaccagg cactggccaa | 900 |
| ctgaacccat cgattcccaa gacctatgaa gtagtcaaga atgtcatcca gggcactatc | 960 |
| gccatgtttc cggattcact ctttcacgga ggagcagatg agatcaattc agactgttgg | 1020 |
| aatactgatc tatcagtcca aaagtttgtt gctagcaatg gaactctcag tcagctacta | 1080 |
| gagaagttta tcaataatac cttacctgaa atcctctcac tcaatcgtac ggtggtctac | 1140 |
| tgggaggatg ttatattgag tggtaatgtg aaagtgaatc catctctgct tcctccacag | 1200 |
| aatgttatta tgcaaacttg gaataatgga ccaaacaata caaagcagct tgtcacttct | 1260 |
| ggctaccgtg tgattgtgtc atctgcagat tactattact tggattgtgg ccatggaagc | 1320 |
| ttcgttggga atgacagccg ctatgatcag ccaccaggta ctgaccaagg caatggcgga | 1380 |
| tcatggtgtg ggcctttcaa gacgtgggaa accatttaca actatgatat aacctacggc | 1440 |
| ctaactgatg aggaggctcc attggtaatt ggaggggaag tagcattatg gtccgaacaa | 1500 |
| gctgattcaa ctgttatgga ctcaaggatt tggccaagag catcagcaat ggcagaagca | 1560 |
| ttgtggtcag gaaatcgtga tgaaacagga atgaagagat atgcagaggc tactgatcga | 1620 |
| ctgaatgaat ggaggtacag aatggttttct agggaatag gtgctgaatc gattcaacca | 1680 |
| ctttggtgtc tcaaaaaccc aggcatgtgt aacacagttc attcatttac tagctgatcc | 1740 |
| ttcatcagtg tctgtaccag tcatttatct gtattatctt ctatattcag atccagttta | 1800 |
| ttattgtaat gttaccttct attgtcacca cattaccatg atttactag gcaaatgaat | 1860 |
| ctgggaattt cttaca | 1876 |

<210> SEQ ID NO 3
<211> LENGTH: 575
<212> TYPE: PRT
<213> ORGANISM: Solanum lycopersicum

<400> SEQUENCE: 3

Met Arg Gly Glu Lys Thr Phe Ser Phe Phe Leu Leu Leu Phe Ile
1               5                   10                  15

Leu Ile Ser Gln Thr Thr Ala Thr Asn Tyr Pro Ile Asn Val Trp Pro
                20                  25                  30

Lys Pro Thr Thr Phe Leu Trp Pro Asn Pro Lys Ser Ile Phe Leu Ser
            35                  40                  45

```
Thr Asn Phe Thr Ile Ser His Pro Tyr His Arg Tyr Leu Thr Pro Ala
 50                  55                  60
Val Asp Arg Tyr Arg His Leu Ile Leu Ser Glu His His Arg Pro Ile
 65                  70                  75                  80
Ile Thr Pro Ala Ile Asn Leu Thr Ser Ser Ile Pro Leu Gln Ser Leu
                 85                  90                  95
Val Ile Ser Val Ser Asp Val Thr Ser Pro Leu Ala His Gly Val Asn
                100                 105                 110
Glu Ser Tyr Ser Leu Ser Thr Pro Ser Asp Gly Ser Ala Ser Ala Tyr
            115                 120                 125
Ile Ser Ala Ala Thr Val Trp Gly Ala Met Arg Gly Leu Glu Thr Phe
130                 135                 140
Ser Gln Leu Val Tyr Gly Asn Pro Thr Arg Val Ser Ala Gly Val Tyr
145                 150                 155                 160
Ile His Asp Leu Pro Ile Phe Thr His Arg Gly Val Met Leu Asp Thr
                165                 170                 175
Ser Arg Asn Phe Tyr Gly Val Asp His Leu Leu Arg Leu Ile Lys Ala
            180                 185                 190
Met Ser Met Asn Lys Leu Asn Val Phe His Trp His Ile Thr Asp Ser
        195                 200                 205
His Ser Phe Pro Leu Val Ile Pro Ser Glu Pro Glu Leu Ala Gly Lys
210                 215                 220
Gly Ala Tyr Ser Asn Glu Met Met Tyr Ser Pro Ala Asp Val Gln Lys
225                 230                 235                 240
Ile Val Glu Tyr Gly Met Glu His Gly Val Arg Val Leu Pro Glu Ile
                245                 250                 255
Asp Met Pro Ala His Thr Gly Ser Trp Ala Glu Ala Tyr Pro Glu Ile
            260                 265                 270
Val Thr Cys Ala Asn Met Phe Trp Trp Pro Ala Gly Ser Ser Pro Ala
        275                 280                 285
Leu Ala Ala Glu Pro Gly Thr Gly Gln Leu Asn Pro Ser Ile Pro Lys
        290                 295                 300
Thr Tyr Glu Val Val Lys Asn Val Ile Gln Gly Thr Ile Ala Met Phe
305                 310                 315                 320
Pro Asp Ser Leu Phe His Gly Gly Ala Asp Glu Ile Asn Ser Asp Cys
                325                 330                 335
Trp Asn Thr Asp Leu Ser Val Gln Lys Phe Val Ala Ser Asn Gly Thr
            340                 345                 350
Leu Ser Gln Leu Leu Glu Lys Phe Ile Asn Asn Thr Leu Pro Glu Ile
        355                 360                 365
Leu Ser Leu Asn Arg Thr Val Val Tyr Trp Glu Asp Val Ile Leu Ser
370                 375                 380
Gly Asn Val Lys Val Asn Pro Ser Leu Leu Pro Pro Gln Asn Val Ile
385                 390                 395                 400
Met Gln Thr Trp Asn Asn Gly Pro Asn Thr Lys Gln Leu Val Thr
                405                 410                 415
Ser Gly Tyr Arg Val Ile Val Ser Ser Ala Asp Tyr Tyr Leu Asp
            420                 425                 430
Cys Gly His Gly Ser Phe Val Gly Asn Asp Ser Arg Tyr Asp Gln Pro
        435                 440                 445
Pro Gly Thr Asp Gln Gly Asn Gly Gly Ser Trp Cys Gly Pro Phe Lys
        450                 455                 460
Thr Trp Glu Thr Ile Tyr Asn Tyr Asp Ile Thr Tyr Gly Leu Thr Asp
```

```
              465                 470                 475                 480
Glu Glu Ala Pro Leu Val Ile Gly Gly Glu Val Ala Leu Trp Ser Glu
                    485                 490                 495

Gln Ala Asp Ser Thr Val Met Asp Ser Arg Ile Trp Pro Arg Ala Ser
                500                 505                 510

Ala Met Ala Glu Ala Leu Trp Ser Gly Asn Arg Asp Glu Thr Gly Met
            515                 520                 525

Lys Arg Tyr Ala Glu Ala Thr Asp Arg Leu Asn Glu Trp Arg Tyr Arg
        530                 535                 540

Met Val Ser Arg Gly Ile Gly Ala Glu Ser Ile Gln Pro Leu Trp Cys
545                 550                 555                 560

Leu Lys Asn Pro Gly Met Cys Asn Thr Val His Ser Phe Thr Ser
                565                 570                 575

<210> SEQ ID NO 4
<211> LENGTH: 1725
<212> TYPE: DNA
<213> ORGANISM: Capsicum annuum

<400> SEQUENCE: 4
```

| | | | | |
|---|---|---|---|---|
| atgagaggag | acacaacatt | cccattcatt | ctttcactat | tcgttatctt cattactcaa | 60 |
| acaatagcta | caaattaccc | aattaatgtc | tggcccaagc | ccacaacatt caattggccc | 120 |
| aacccaaaaa | tccatcttcc | tctcccaac | ttcaccatct | cccacccgac ccaccgttac | 180 |
| ctaactccca | ccgtttaccg | gtaccgccgt | ctcatcctct | ccgagcacta ccgccacatc | 240 |
| atcactccgt | cgatcaacct | gacgtcatca | actccgttac | aacacctcat catctccgtc | 300 |
| tccgacgtca | cttcaccgtt | atctcacggc | gtcaacgaat | cctactctct ctccacgcct | 360 |
| aacggttctt | ccgccgccta | cataactgcc | ggtaccgtat | gggagccat gagaggactc | 420 |
| gagacattct | cacagctcgt | gtacggaaac | cctactcgag | tcgccgcagg cgtgtacata | 480 |
| tccgatctgc | cgattttcac | tcaccgtggt | gtgatgttgg | acacttcgag aaacttctac | 540 |
| ggagtagatg | atttgttgag | gcttatcaaa | gctatgagta | tgaacaagct gaatgttttt | 600 |
| cactggcaca | taactgattc | acattcgttt | ccgcttgtgg | ttccatcgga gccggagctt | 660 |
| gccggaaaag | gagcatacgg | caatgagatg | atgtactcgc | cggcggatgt ggagaagatt | 720 |
| gtggaatttg | gaatggaaca | tggagttagg | gttttacctg | agattgatat gcccgcacat | 780 |
| acgggatcat | gggctgaagc | ttaccctgag | attatcactt | gtgcaaatat gttctggtgg | 840 |
| cctgctggaa | atagtccagc | tcttgcagct | gaaccaggca | ctggtcaact gaaccctttg | 900 |
| attcccaaaa | cctatgaagt | agtcaagaat | gtcatccacg | ataccatcgc catgtttcca | 960 |
| gattccctct | ttcacggggg | agcagatgag | atcaattcag | catgttggaa tactgatcca | 1020 |
| tcaatccaaa | cgtttgttgc | tagcaatgga | actcagagtc | agctactcga atgtttatc | 1080 |
| aataatacct | acctgaaat | cctctcactc | aaccgtactg | tggtctactg ggaggatgtt | 1140 |
| atattgagtg | ctaatgtgaa | ggtggatcca | tctctgcttt | cgccacaaca tgttatcatg | 1200 |
| caaacttgga | ataatggacc | aagcaataca | aagcagctcg | tcacttctgg gtaccgtgtc | 1260 |
| attgtgtcat | ctgcagatta | ctattacttg | gattgtggcc | atgggagttt cgttggaaat | 1320 |
| gacagccgct | atgaccagcc | cccaggtact | gaccaaggca | atggtggatc ctggtgtgga | 1380 |
| cctttcaaga | cctgggaaac | catttacaac | tatgatataa | cctatggtct gactgataag | 1440 |
| gaggctcaat | tggtaatcgg | aggggaagta | gcattatggt | ccgaacaagc tgattcaact | 1500 |
| gttatggact | cacgaatttg | gcctagagca | tcagcaatgg | cagagacatt gtggtcaggg | 1560 |

-continued

```
aattgcgatg aaacaggaat gaagagatat gcagaggcta ctgatcgact gactgaatgg    1620
aggtacagaa tggttgctag gggaataggt gctgaaccta ttcaaccact ttggtgtgtc    1680
aaaaactcag gaatgtgtaa cacagttcat tcatttacta gctga                    1725
```

<210> SEQ ID NO 5
<211> LENGTH: 574
<212> TYPE: PRT
<213> ORGANISM: Capsicum annuum

<400> SEQUENCE: 5

| Met | Arg | Gly | Asp | Thr | Thr | Phe | Pro | Phe | Ile | Leu | Ser | Leu | Phe | Val | Ile |
|---|---|---|---|---|---|---|---|---|---|---|---|---|---|---|---|
| 1 | | | | 5 | | | | | 10 | | | | | 15 | |

| Phe | Ile | Thr | Gln | Thr | Ile | Ala | Thr | Asn | Tyr | Pro | Ile | Asn | Val | Trp | Pro |
| | | | 20 | | | | | 25 | | | | | 30 | | |

| Lys | Pro | Thr | Thr | Phe | Asn | Trp | Pro | Asn | Pro | Lys | Ile | His | Leu | Pro | Leu |
| | | | 35 | | | | 40 | | | | | 45 | | | |

| Pro | Asn | Phe | Thr | Ile | Ser | His | Pro | Thr | His | Arg | Tyr | Leu | Thr | Pro | Thr |
| | 50 | | | | | 55 | | | | | 60 | | | | |

| Val | Tyr | Arg | Tyr | Arg | Arg | Leu | Ile | Leu | Ser | Glu | His | Tyr | Arg | His | Ile |
| 65 | | | | | 70 | | | | | 75 | | | | | 80 |

| Ile | Thr | Pro | Ser | Ile | Asn | Leu | Thr | Ser | Ser | Thr | Pro | Leu | Gln | His | Leu |
| | | | | 85 | | | | | 90 | | | | | 95 | |

| Ile | Ile | Ser | Val | Ser | Asp | Val | Thr | Ser | Pro | Leu | Ser | His | Gly | Val | Asn |
| | | | | 100 | | | | | 105 | | | | | 110 | |

| Glu | Ser | Tyr | Ser | Leu | Ser | Thr | Pro | Asn | Gly | Ser | Ser | Ala | Ala | Tyr | Ile |
| | | | 115 | | | | | 120 | | | | | 125 | | |

| Thr | Ala | Gly | Thr | Val | Trp | Gly | Ala | Met | Arg | Gly | Leu | Glu | Thr | Phe | Ser |
| | 130 | | | | | 135 | | | | | 140 | | | | |

| Gln | Leu | Val | Tyr | Gly | Asn | Pro | Thr | Arg | Val | Ala | Ala | Gly | Val | Tyr | Ile |
| 145 | | | | | 150 | | | | | 155 | | | | | 160 |

| Ser | Asp | Leu | Pro | Ile | Phe | Thr | His | Arg | Gly | Val | Met | Leu | Asp | Thr | Ser |
| | | | | 165 | | | | | 170 | | | | | 175 | |

| Arg | Asn | Phe | Tyr | Gly | Val | Asp | Asp | Leu | Leu | Arg | Leu | Ile | Lys | Ala | Met |
| | | | 180 | | | | | 185 | | | | | 190 | | |

| Ser | Met | Asn | Lys | Leu | Asn | Val | Phe | His | Trp | His | Ile | Thr | Asp | Ser | His |
| | | 195 | | | | | 200 | | | | | 205 | | | |

| Ser | Phe | Pro | Leu | Val | Val | Pro | Ser | Glu | Pro | Glu | Leu | Ala | Gly | Lys | Gly |
| | 210 | | | | | 215 | | | | | 220 | | | | |

| Ala | Tyr | Gly | Asn | Glu | Met | Met | Tyr | Ser | Pro | Ala | Asp | Val | Glu | Lys | Ile |
| 225 | | | | | 230 | | | | | 235 | | | | | 240 |

| Val | Glu | Phe | Gly | Met | Glu | His | Gly | Val | Arg | Val | Leu | Pro | Glu | Ile | Asp |
| | | | | 245 | | | | | 250 | | | | | 255 | |

| Met | Pro | Ala | His | Thr | Gly | Ser | Trp | Ala | Glu | Ala | Tyr | Pro | Glu | Ile | Ile |
| | | | 260 | | | | | 265 | | | | | 270 | | |

| Thr | Cys | Ala | Asn | Met | Phe | Trp | Trp | Pro | Ala | Gly | Asn | Ser | Pro | Ala | Leu |
| | | 275 | | | | | 280 | | | | | 285 | | | |

| Ala | Ala | Glu | Pro | Gly | Thr | Gly | Gln | Leu | Asn | Pro | Leu | Ile | Pro | Lys | Thr |
| | 290 | | | | | 295 | | | | | 300 | | | | |

| Tyr | Glu | Val | Val | Lys | Asn | Val | Ile | His | Asp | Thr | Ile | Ala | Met | Phe | Pro |
| 305 | | | | | 310 | | | | | 315 | | | | | 320 |

| Asp | Ser | Leu | Phe | His | Gly | Gly | Ala | Asp | Glu | Ile | Asn | Ser | Ala | Cys | Trp |
| | | | | 325 | | | | | 330 | | | | | 335 | |

| Asn | Thr | Asp | Pro | Ser | Ile | Gln | Thr | Phe | Val | Ala | Ser | Asn | Gly | Thr | Gln |

```
                340             345             350
Ser Gln Leu Leu Glu Met Phe Ile Asn Asn Thr Leu Pro Glu Ile Leu
            355                 360                 365

Ser Leu Asn Arg Thr Val Val Tyr Trp Glu Asp Val Ile Leu Ser Ala
            370                 375                 380

Asn Val Lys Val Asp Pro Ser Leu Leu Ser Pro Gln His Val Ile Met
385                 390                 395                 400

Gln Thr Trp Asn Asn Gly Pro Ser Asn Thr Lys Gln Leu Val Thr Ser
                405                 410                 415

Gly Tyr Arg Val Ile Val Ser Ser Ala Asp Tyr Tyr Leu Asp Cys
                420                 425                 430

Gly His Gly Ser Phe Val Gly Asn Asp Ser Arg Tyr Asp Gln Pro Pro
            435                 440                 445

Gly Thr Asp Gln Gly Asn Gly Gly Ser Trp Cys Gly Pro Phe Lys Thr
            450                 455                 460

Trp Glu Thr Ile Tyr Asn Tyr Asp Ile Thr Tyr Gly Leu Thr Asp Lys
465                 470                 475                 480

Glu Ala Gln Leu Val Ile Gly Gly Glu Val Ala Leu Trp Ser Glu Gln
                485                 490                 495

Ala Asp Ser Thr Val Met Asp Ser Arg Ile Trp Pro Arg Ala Ser Ala
            500                 505                 510

Met Ala Glu Thr Leu Trp Ser Gly Asn Cys Asp Glu Thr Gly Met Lys
            515                 520                 525

Arg Tyr Ala Glu Ala Thr Asp Arg Leu Thr Glu Trp Arg Tyr Arg Met
            530                 535                 540

Val Ala Arg Gly Ile Gly Ala Glu Pro Ile Gln Pro Leu Trp Cys Val
545                 550                 555                 560

Lys Asn Ser Gly Met Cys Asn Thr Val His Ser Phe Thr Ser
                565                 570

<210> SEQ ID NO 6
<211> LENGTH: 37
<212> TYPE: DNA
<213> ORGANISM: Artificial Sequence
<220> FEATURE:
<223> OTHER INFORMATION: Synthetic Primer

<400> SEQUENCE: 6
ggccacgcgt cgactagtac tttttttttt tttttt                              37

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (6)..(6)
<223> OTHER INFORMATION: n represents inosine
<220> FEATURE:
<221> NAME/KEY: misc_feature
<222> LOCATION: (15)..(15)
<223> OTHER INFORMATION: n represents inosine

<400> SEQUENCE: 7
aarytnatgt tytcnytggc a                                              21

<210> SEQ ID NO 8
<211> LENGTH: 20
```

```
<212> TYPE: DNA
<213> ORGANISM: Artificial Sequence
<220> FEATURE:
<223> OTHER INFORMATION: Synthetic Primer

<400> SEQUENCE: 8
ggccacgcgt cgactagtac                                              20

<210> SEQ ID NO 9
<211> LENGTH: 53
<212> TYPE: DNA
<213> ORGANISM: Artificial Sequence
<220> FEATURE:
<223> OTHER INFORMATION: Synthetic Primer

<400> SEQUENCE: 9
ggggacaagt ttgtacaaaa aagcaggcta tgagaggaga gaaaacattc tcc         53

<210> SEQ ID NO 10
<211> LENGTH: 54
<212> TYPE: DNA
<213> ORGANISM: Artificial Sequence
<220> FEATURE:
<223> OTHER INFORMATION: Synthetic Primer

<400> SEQUENCE: 10
gggaccactt tgtacaagaa agctgggtgc tagtaaatga atgacctgtg ttac        54

<210> SEQ ID NO 11
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 11
tatgttctgg tggcccg                                                 17

<210> SEQ ID NO 12
<211> LENGTH: 18
<212> TYPE: DNA
<213> ORGANISM: Artificial Sequence
<220> FEATURE:
<223> OTHER INFORMATION: Synthetic Primer

<400> SEQUENCE: 12
tctgctcctc cgtgaaag                                                18

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
ttatcaccat tggtgctgag                                              20

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer

<400> SEQUENCE: 14
```
cgatgtttcc atacagatcc tt                                              22

<210> SEQ ID NO 15
<211> LENGTH: 36
<212> TYPE: DNA
<213> ORGANISM: Artificial Sequence
<220> FEATURE:
<223> OTHER INFORMATION: Synthetic Primer

<400> SEQUENCE: 15
ccgctcgaga agcagtggta tcaacgcaga gtacgc                               36

<210> SEQ ID NO 16
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 16
ccgctcgagg agaaaaaaat gagaggagag aaaac                                35

<210> SEQ ID NO 17
<211> LENGTH: 32
<212> TYPE: DNA
<213> ORGANISM: Artificial Sequence
<220> FEATURE:
<223> OTHER INFORMATION: Synthetic Primer

<400> SEQUENCE: 17
ggaattccag ccttaacaag tgatcgactc cg                                   32

<210> SEQ ID NO 18
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 18
gctctagaaa gcagtggtat caacgcagag tacgc                                35

<210> SEQ ID NO 19
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 19
gctctagaga gaaaaaaatg agaggagaga aaac                                 34

<210> SEQ ID NO 20
<211> LENGTH: 34
<212> TYPE: DNA
<213> ORGANISM: Artificial Sequence
<220> FEATURE:
<223> OTHER INFORMATION: Synthetic Primer

<400> SEQUENCE: 20
cccaagcttc agccttaaca agtgatcgac tccg                                 34

<210> SEQ ID NO 21
<211> LENGTH: 30
<212> TYPE: DNA
<213> ORGANISM: Artificial Sequence -continued

```
<220> FEATURE:
<223> OTHER INFORMATION: Synthetic Primer

<400> SEQUENCE: 21
ccgctcgagc cgtgtgattg tgtcatctgc                                      30

<210> SEQ ID NO 22
<211> LENGTH: 32
<212> TYPE: DNA
<213> ORGANISM: Artificial Sequence
<220> FEATURE:
<223> OTHER INFORMATION: Synthetic Primer

<400> SEQUENCE: 22
ggaattcgta agaaattccc agattcattt gc                                   32

<210> SEQ ID NO 23
<211> LENGTH: 29
<212> TYPE: DNA
<213> ORGANISM: Artificial Sequence
<220> FEATURE:
<223> OTHER INFORMATION: Synthetic Primer

<400> SEQUENCE: 23
gctctagacc gtgtgattgt gtcatctgc                                       29

<210> SEQ ID NO 24
<211> LENGTH: 33
<212> TYPE: DNA
<213> ORGANISM: Artificial Sequence
<220> FEATURE:
<223> OTHER INFORMATION: Synthetic Primer

<400> SEQUENCE: 24
cgggatccgt aagaaattcc cagattcatt tgc                                  33

<210> SEQ ID NO 25
<211> LENGTH: 32
<212> TYPE: DNA
<213> ORGANISM: Artificial Sequence
<220> FEATURE:
<223> OTHER INFORMATION: Synthetic Primer

<400> SEQUENCE: 25
gctctagaat gagaggagag aaaacattct cc                                   32

<210> SEQ ID NO 26
<211> LENGTH: 23
<212> TYPE: DNA
<213> ORGANISM: Artificial Sequence
<220> FEATURE:
<223> OTHER INFORMATION: Synthetic Primer

<400> SEQUENCE: 26
tcagctagta aatgaatgaa ctg                                             23

<210> SEQ ID NO 27
<211> LENGTH: 24
<212> TYPE: DNA
<213> ORGANISM: Artificial Sequence
<220> FEATURE:
<223> OTHER INFORMATION: Synthetic Primer

<400> SEQUENCE: 27
atgagaggag agaaaacatt ctcc                                            24
```

```
<210> SEQ ID NO 28
<211> LENGTH: 33
<212> TYPE: DNA
<213> ORGANISM: Artificial Sequence
<220> FEATURE:
<223> OTHER INFORMATION: Synthetic Primer

<400> SEQUENCE: 28
gctctagagt aagaaattcc cagattcatt tgc                          33
```